(12) United States Patent
Lu et al.

(10) Patent No.: US 12,409,173 B2
(45) Date of Patent: Sep. 9, 2025

(54) REPURPOSING FDA-APPROVED DRUGS AS A NOVEL CANCER THERAPEUTIC AVENUE THROUGH INHIBITION OF PRMT5

(71) Applicant: THE TRUSTEES OF INDIANA UNIVERSITY, Bloomington, IN (US)

(72) Inventors: Tao Lu, Carmel, IN (US); Matthew Martin, Indianapolis, IN (US); Lakshmi Milind Prabhu, Ridgefield, CT (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 604 days.

(21) Appl. No.: 17/782,920

(22) PCT Filed: Dec. 31, 2020

(86) PCT No.: PCT/US2020/067694
§ 371 (c)(1),
(2) Date: Jun. 6, 2022

(87) PCT Pub. No.: WO2021/138578
PCT Pub. Date: Jul. 8, 2021

(65) Prior Publication Data
US 2023/0346761 A1 Nov. 2, 2023

Related U.S. Application Data

(60) Provisional application No. 62/965,256, filed on Jan. 24, 2020, provisional application No. 62/955,930, filed on Dec. 31, 2019.

(51) Int. Cl.
*A61K 31/4453* (2006.01)
*A61K 31/4184* (2006.01)
*A61K 45/06* (2006.01)
*A61P 35/00* (2006.01)

(52) U.S. Cl.
CPC ...... *A61K 31/4453* (2013.01); *A61K 31/4184* (2013.01); *A61K 45/06* (2013.01); *A61P 35/00* (2018.01)

(58) Field of Classification Search
CPC ............ A61K 31/4453; A61K 31/4184; A61K 45/06; A61P 35/00
See application file for complete search history.

(56) References Cited

U.S. PATENT DOCUMENTS

2010/0029734 A1   2/2010   White et al.

FOREIGN PATENT DOCUMENTS

| CN | 108379265 A | 8/2018 | |
|---|---|---|---|
| JP | 2007077095 A | 3/2007 | |
| WO | WO-2013004999 A1 * | 1/2013 | ........... A61K 31/045 |
| WO | 2018081451 A1 | 5/2018 | |
| WO | 2019094312 A1 | 5/2019 | |
| WO | 2019/216360 A1 | 11/2019 | |
| WO | 2019246557 A1 | 12/2019 | |

OTHER PUBLICATIONS

Extended Search Report for copending European Application No. 20909822.7, mailed Jan. 2, 2024.
Kharkar Prashant S et al.: "Drug repurposing for breast cancer: Preliminary medicinal chemistry investigations and future perspectives", Journal of the Indian Chemical Society, vol. 97, No. 8, Aug. 1, 2020 (Aug. 1, 2020), pp. 1245-1250, XP093109250, IN, ISSN: 0019-4522.
Prabhu Lakshmi et al.: "Inhibition of PRMT5 by market drugs as a novel cancer therapeutic avenue", Genes & Diseases, vol. 10, No. 1, Apr. 13, 2022 (Apr. 13, 2022), pp. 267-283, XP093109254, NL, ISSN: 2352-3042, DOI: 10.1016/j.gendis.2022.04.001.
PCT International Search Report and Written Opinion completed by the ISA/US on Mar. 10, 2021 and issued in connection with PCT/US2020/067694.
Luo et al. "Ang iotensin II and NADPH Oxidase Increase ADMA in Vascular Smooth Muscle Cells," Hypertension, Aug. 9, 2010 (Aug. 9, 2010), vol. 56, Iss. 3, pp. 498-504. entire document.

\* cited by examiner

*Primary Examiner* — James H Alstrum-Acevedo
*Assistant Examiner* — Justin Christopher Sanchez
(74) *Attorney, Agent, or Firm* — Barnes & Thornburg LLP

(57) ABSTRACT

Disclosed herein are methods of inhibiting a protein arginine methyltransferase by contacting the methyltransferase with a compound selected from the group consisting of cloperastine hydrochloride, candesartan cilexetil, or analog of such compounds, and combinations thereof. One embodiment of the present disclosure is directed to a method of identifying compounds that inhibit PRMT5 methyltransferase activity.

17 Claims, 32 Drawing Sheets
Specification includes a Sequence Listing.

Summary of AlphaLISA $IC_{50}$

| Drug name | $IC_{50}$ |
|---|---|
| Clo | 27µM |
| Can | 33µM |

Cloperastine, µM
PANC1

| Drug name | Cell Line | Cloperastine $IC_{50}$, μM | Candesartan, $IC_{50}$, μM |
|---|---|---|---|
| PDAC | PANC1 | 30 | 18 |
| | MiaPaCa2 | 30 | 23 |
| | AsPC1 | 29 | 18 |
| CRC | HT29 | 34 | 15 |
| | HCT116 | 32 | 15 |
| | DLD1 | 18 | 17 |
| BC | MDA-MB-231 | 29 | 18 |
| | BT20 | 26 | 20 |

Abbreviations: BC, breast cancer; CRC, colorectal cancer; IC, inhibitory concentration; PDAC, pancreatic ductal adenocarcinoma.

SEQUENCE LISTING

```
<160> NUMBER OF SEQ ID NOS: 7

<210> SEQ ID NO 1
<211> LENGTH: 26
<212> TYPE: PRT
<213> ORGANISM: Homo sapiens

<400> SEQUENCE: 1

Ser Gly Arg Gly Lys Gly Gly Lys Gly Leu Gly Lys Gly Gly Ala Lys
1               5                   10                  15

Arg His Arg Lys Val Leu Arg Gly Gly Lys
            20                  25

<210> SEQ ID NO 2
<211> LENGTH: 22
<212> TYPE: DNA
<213> ORGANISM: Artificial Sequence
<220> FEATURE:
<223> OTHER INFORMATION: PCR primer

<400> SEQUENCE: 2
ccatcaccat cttccaggag cg                                              22

<210> SEQ ID NO 3
<211> LENGTH: 21
<212> TYPE: DNA
<213> ORGANISM: Artificial Sequence
<220> FEATURE:
<223> OTHER INFORMATION: PCR Primer

<400> SEQUENCE: 3
tcctgatttc tgcagctctg t                                               21

<210> SEQ ID NO 4
<211> LENGTH: 25
<212> TYPE: DNA
<213> ORGANISM: Artificial Sequence
<220> FEATURE:
<223> OTHER INFORMATION: PCR Primer

<400> SEQUENCE: 4
gacgccctca atcaaagtat aattc                                           25

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
agagatgatg accctttggg c                                               21
```

```
<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
aaatttgggg tggaaaggtt                                          20

<210> SEQ ID NO 7
<211> LENGTH: 25
<212> TYPE: DNA
<213> ORGANISM: Artificial Sequence
<220> FEATURE:
<223> OTHER INFORMATION: PCR Primer

<400> SEQUENCE: 7
tcaaatttca ctgcttcatc cagat                                    25
```

REPURPOSING FDA-APPROVED DRUGS AS A NOVEL CANCER THERAPEUTIC AVENUE THROUGH INHIBITION OF PRMT5

CROSS REFERENCE TO RELATED APPLICATIONS

This application is a U.S. national counterpart application of international application serial No. PCT/US2020/067694 filed Dec. 31, 2020, which claims priority to U.S. Provisional Patent Application Nos. 62/955,930 filed on Dec. 31, 2019 and 62/965,256, filed Jan. 24, 2020, the disclosures of which are hereby expressly incorporated by reference in their entireties.

STATEMENT REGARDING FEDERALLY SPONSORED RESEARCH AND DEVELOPMENT

This invention was made with government support under TR001108 awarded by National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 2 kilobytes ACII (Text) file named "332674SeqListing_ST25.txt," created on Dec. 24, 2020.

BACKGROUND OF THE DISCLOSURE

Repurposing of Food and Drug Administration (FDA)-approved drugs for indications apart from their primary intended therapeutic purpose has been a popular method in drug discovery and development. The gain in popularity for adopting this method is two-fold: 1. the safety, efficacy, formulation and toxicity profiles of a clinically approved drug are well established for a particular indication. This allows for valuable resources such as time and money to be saved by streamlining studies for testing a new indication based on existing data, such as preventing the need to conduct phase I clinical studies to understand its safety in humans. Thus, approval of repurposed drugs is about 3-12 years faster and at about 50% lower cost in comparison to their de novo counterparts 2. Compounds that were shelved in earlier clinical trials due to unfavorable results could still be potentially developed for other indications, thus preventing wastage of resources involved in unsuccessful clinical trials.

Several successful examples of drugs that were in development or approved for treatment which were then repositioned for novel indications have been demonstrated over the years. Perhaps, the most famous example is Sildenafil (Viagra®), a phosphodiesterase 5 inhibitor first developed by Pfizer that is currently used to treat erectile dysfunction in adult males. Sildenafil was originally being developed to treat hypertension in the mid 1980s, with the aim of vasodilating arteries and lessening blood pressure. Interestingly, in clinical trials, researchers observed that this drug was significantly more effective in treating erectile dysfunction than heart disease, thereby repositioning it for a new indication. Viagra is currently prescribed to millions of people and has generated billions of dollars in revenue since it was approved by FDA in 1998. Interestingly, a further repurposing of Viagra might be on the horizon since new trials have shown its potential as an anti-cancer drug. If shown to been effective, it will severely shorten the approval process for the new indication, while at the same time providing a cost-effective treatment option in cancers. Sildenafil is just one of the many instances that have shown a successful repurposing of already approved drugs for cancers amongst other diseases. One focus of the invention is on adapting FDA-approved drugs for potentially treating some of the deadliest cancers today namely, pancreatic ductal adenocarcinoma (PDAC), colorectal cancer (CRC) and breast cancer (BC).

CRC and PDAC are the third and fourth leading causes of deaths in men and women combined in the United States respectively. Similarly, breast cancer is the second leading cause of death for women in the US, amounting to 14% of the total cancer-related deaths in females. The triple-negative subtype accounts for about 15% of the cases and is marked by shorter survival and higher chance of recurrence than the other subtypes. For these three cancer types, chemotherapy and certain targeted therapies are currently available in the clinic. At the same time, several dozen novel small molecules/biologics are being developed, with some reaching clinical trials after several years in the discovery phase of drug development. Despite this, mortality rates due to these cancers continue to rise rapidly. Furthermore, the budget required to develop and bring these drugs to market as well as treatment cost to suffering patients continues to be unimaginably high, creating a considerable challenge for developing cost-effective therapies at a rapid pace. It is imperative to design studies and identify critical factors that can be a subject of effective therapeutic strategies. Even more importantly, it would be highly beneficial to shorten the FDA approval process so that these treatments speedily reach the clinic while at the same time are effective, safe and economical.

Posttranslational modifications (PTMs) regulate protein function in eukaryotes and have been shown to play a ubiquitous role in a variety of cellular functions. In the past decade, research has greatly advanced the understanding of the role of PTMs of various signaling molecules that lead to the development of a variety of diseases, including cancers. Methylation of lysines and arginines are one of the most critical PTMs seen in nature and are implicated in a number of cellular processes, such as DNA damage and repair, gene transcription and translation, and protein subcellular localization and translocation. Arginine methylation is carried out by a group of enzymes termed protein arginine methyltransferases. Amongst this family, protein arginine methyltransferase 5 (PRMT5) has been implicated in the development of a wide range of diseases. For example, the expression of PRMT5 is upregulated in a variety of cancers (e.g., liver cancer, pancreatic cancer, colon cancer, breast cancer, prostate cancer, and lung cancer, as well as lymphoma and melanoma), neurodegenerative disorders, inflammatory diseases, metabolic disorders, cardiovascular diseases, autoimmune disorders, and blood disorders.

PRMT5 is an activator of the nuclear factor κB (NF-κB) via dimethylating arginine 30 of its p65 subunit. NF-κB is a critical eukaryotic transcription factor whose family consists of five members: RelA (p65), RelB, cRel, NF-κBd1 (p50 and its precursor p105) and NF-κB2 (p52 and its precursor p100). NF-κB signaling can be classified into canonical and non-canonical pathways. The canonical pathway has been well established as a key contributor to development of both pancreatic ductal adenocarcinoma (PDAC), colorectal cancer (CRC), and breast cancer (BC). In this pathway, inhibitor of κB (IκBα) sequesters p65:p50 heterodimer in an inactive state in the cytoplasm. When a cell receives extracellular signals, such as stress or pro-inflammatory cytokines, IκB kinase phosphorylates IκBα, this leads to the degradation of IκB and release of the p65:p50 complex and activation of NF-κB target genes. A number of these downstream NF-κB target genes have been implicated in a wide range of diseases including cancer, neurodegenerative disorders, inflammatory diseases, metabolic disorders, cardiovascular diseases, autoimmune disorders, and blood disorders. Increased NF-κB activation is shown to be associated with a poor disease prognosis, and linked to developing resistance against chemotherapy.

Since PRMT5 is a novel activator of NF-κB, inhibition of PRMT5 using small molecule inhibitors has been reported to slow tumor growth. Thus, PRMT5 has immense potential to be used as a therapeutic target in these cancers. In this regard, an amplified luminescent proximity homogenous assay-linked immunosorbent assay (AlphaLISA)-based high-throughput screen (HTS) was developed to screen for FDA-approved drugs with anti-PRMT5 activity. A need exists to develop PRMT5 as a viable therapeutic target with a much shorter path of approval as compounds go through clinical trials and into the clinic, if found promising. In this process, the FDA-approved drugs, Cloperastine hydrochloride (Clo) and Candesartan cilexetil (Can) were identified as having anti-PRMT5 activity. These FDA-approved compounds were tested for efficacy in reducing the cancer phenotype as well as for selectivity in inhibiting PRMT5 methyltransferase activity by checking for effect of these drugs on its substrate, i.e. NF-κB's activation. These studies reiterate the promising nature of repurposing FDA approved drugs to identify novel targets (for instance, PRMT5) and employ them for use in newer indications, such as the cancer subtypes described herein.

SUMMARY

One embodiment of the present disclosure is directed to a method of identifying compounds that inhibit PRMT5 methyltransferase activity. In one embodiment a system for quantitating PRMT5 enzymatic activity in a solution is provided. In one embodiment the system comprises 1) a PRMT5 substrate, that has been modified by the covalent linkage of a biotin molecule, optionally at the N-terminus of the PRMT5 substrate, 2) a methyl donor, optionally S-adenosyl-1-methionine (SAM), 3) a solid substrate acceptor and 4) a solid substrate donor. In one embodiment the PRMT5 substrate is a protein such as histone H4 peptide that is unmethylated at the arginine (R) located at position 3 (unmeH4R3). The solid substrate donor component of the system comprises a solid support with a covalently linked streptavidin tag and a donor fluorophore or donor photoreactive element capable of producing a signal upon excitation at 680 nm. The solid substrate acceptor component of the system comprises a solid support with a covalently linked ligand that specifically binds to the PRMT5 substrate when the substrate is in its methylated form and a donor fluorophore or donor photoreactive element capable of producing a signal when stimulated by the signal produced by the donor fluorophore or donor photoreactive element. The signal produced by the solid substrate acceptor is dependent on its proximity to the signal producing solid substrate donor substrate such that the solid substrate acceptor will only effectively emit a signal when the solid substrate acceptor and the solid substrate donor are brought into proximity by the binding of the ligand to the methylated PRMT5 substrate, thus allowing for quantifying PRMT5 methyltransferase activity under different conditions.

In accordance with one embodiment the system for quantitating PRMT5 enzymatic activity is placed in contact with PRMT5 in the presence or absence of a test compound to see if the test compound inhibits PRMT5's ability to methylate the PRMT5 substrate.

In accordance with one embodiment inhibitors of PRMT5 activity, and more particularly inhibition of PRMT5's ability to methylate PRMT5 substrates, are provided. In one embodiment the PRMT5 inhibitory compounds are selected from Cloperastine hydrochloride (Clo) and Candesartan cilexetil (Can) and analogs thereof. As disclosed herein, Cloperastine hydrochloride (Clo) and Candesartan cilexetil (Can) show higher anti-tumor efficacy than the commercial PRMT5 inhibitor, EPZ015666 in both PDAC, CRC and BC. The structure of Cloperastine (Clo) and Candesartan (Can) is provided as follows:

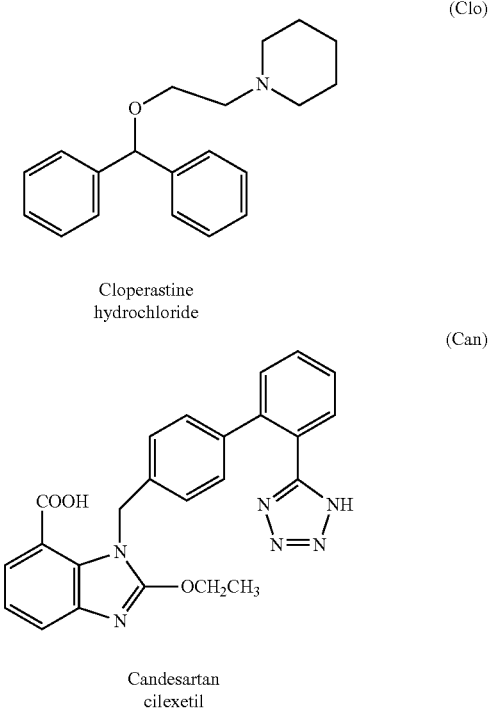

In accordance with one embodiment a method of inhibiting a protein arginine methyltransferase (PRMT) is provided wherein the method comprises the step of contacting the PRMT with a compound selected from the group consisting of cloperastine hydrochloride, candesartan cilexetil and PRMT inhibiting analogs of cloperastine hydrochloride and candesartan cilexetil that retain the parent compound's ability to inhibit arginine methyltransferase activity. In one embodiment the inhibition is conducted by contacting the PRMT with both cloperastine hydrochloride and candesartan cilexetil. In one embodiment the inhibition takes place within a cell after the cell is contacted with cloperastine hydrochloride and/or candesartan cilexetil.

In one embodiment the method of inhibiting a PRMT (optionally wherein the arginine methyl transferase is protein arginine methyltransferase 5 (PRMT5)) in a subject's cells comprises administered a pharmaceutical composition comprising a compound selected from the group consisting of cloperastine hydrochloride, candesartan cilexetil and PRMT inhibiting analogs of cloperastine hydrochloride and candesartan cilexetil to said patient. In one embodiment the pharmaceutical composition comprises cloperastine hydrochloride and/or candesartan cilexetil. In one embodiment the pharmaceutical composition is administered locally by injection into a target tissue. In one embodiment the pharmaceutical composition is administered systemically (e.g., by intravenous injection or by oral administration).

In one embodiment a pharmaceutical composition is provided comprising cloperastine hydrochloride, candesartan cilexetil and a pharmaceutical acceptable carrier. In one embodiment the pharmaceutical composition further comprises an antitumor agent, including for example a chemotherapeutic agent or immunotherapeutic agent. In one embodiment the chemotherapeutic agent is selected from an alkylating agent, an antimetabolite, a topoisomerase inhibitor, a cytotoxic antibiotic, and a mitotic inhibitor.

In one embodiment the pharmaceutical compositions disclosed herein are used to treat a PRMT-mediated disorder, wherein the treatment comprises the step of administering to a subject in need thereof a therapeutically effective amount of a compound selected from the group consisting of cloperastine hydrochloride, candesartan cilexetil and combinations thereof. In one embodiment the PRMT-mediated disorder is associated with excessive PRMT5 activity or high level of expression, and in a further embodiment the methyl transferase-mediated disorder is a cancer, neurodegenerative disorder, such as Alzheimer's disease, cardiovascular disease, such as atherosclerosis, or diabetes, drug addiction, inflammation, etc., all the disorders that are PRMT related.

BRIEF DESCRIPTION OF THE DRAWINGS

FIG. 1A), colorectal cancer (CRC; FIG. 1B) and breast cancer (BC; FIG. 1C). patient cohorts respectively, denoting that patient survival negatively correlated with PRMT5 expression in these groups of patients.

FIG. 2 illustrates the principle of AlphaLISA technique adapted to HTS. Biotinylated histone H4 (a well-known PRMT5 substrate) was mixed with methyl donor, S-adenosyl-1-methionine (SAM) and PRMT5 enzyme. Symmetric dimethylation of third arginine (R3) of H4R3 by PRMT5 on biotin-H4 is recognized by Acceptor beads with an antibody tag specific for this methylation site. Furthermore, Donor beads have a streptavidin tag that bind to biotin tag on H4. Excitation at 680 nm induces Donor beads to emit a singlet oxygen, which is accepted by Acceptor beads bound to the dimethylated site to emit a chemiluminescent signal, thus allowing for quantifying PRMT5 methyltransferase activity.

FIG. 3C presents a table summarizing AlphaLISA $IC_{50}$ values for Clo and Can.

FIG. 4Q is a summary table listing $IC_{50}$ values from FIGS. 4A-4P.

FIGS. 9A-9C are graphs demonstrating significant inhibition of xenograft tumor growth by Clo in pancreatic cancer (PDAC) model (FIG. 9A), colon cancer (CRC) model (FIG. 9B), and breast cancer (BC) model (FIG. 9C). NSG mice (5-6 weeks old) were xenografted with PANC-1 cells (FIG. 9A), or HT29 cells (FIG. 9B), or MCF7 cell (FIG. 9C). Once the volumes of xenografts reached 50-70 mm$^3$, mice were treated with vehicle control (10% DMSO, 20% PEG400, 5% Tween 80 and 65% sterile water), or 100 mg/kg Clo dissolved in the vehicle, through oral gavage (P.O.) daily. FIGS. 9D-9F provide data on the body weight measurement over time of the treated animals. No significant changes in body weight were observed over the course of treatment in either the PANC1, (FIG. 9D), HT29 (FIG. 9E), or MCF7 (FIG. 9F) model after treatment with 100 mg/kg of Clo as compared to the vehicle control group. N=5 mice/group (For PDAC and CRC models, male mice were used; For BC model, female mice were used). *p<0.05 100 mg/kg Clo vs. vehicle control.

FIGS. 10A-10C are a graphs demonstrating significant inhibition of xenograft tumor growth by Can in pancreatic cancer (PDAC) model (FIG. 10A), colon cancer (CRC) model (FIG. 10B), and breast cancer (BC) model (FIG. 10C). NSG mice (5-6 weeks old) were xenografted with PANC-1 cells (FIG. 10A), or HT29 cells (FIG. 10B), or MCF7 cell (FIG. 10C). Once the volumes of xenografts reached 50-70 mm$^3$, mice were treated with vehicle control (10% DMSO, 20% PEG400, 5% Tween 80 and 65% sterile water), or 100 mg/kg Can dissolved in the vehicle, through oral gavage (P.O.) daily. FIGS. 10D-10F provide data on the body weight measurement over time of the treated animals. No significant changes in body weight were observed over the course of treatment in either the PANC1 (FIG. 10D), HT29 (FIG. 10E), or MCF7 (FIG. 10F) model after treatment with 100 mg/kg of Can as compared to the vehicle control group. N=5 mice/group (For PDAC and CRC models, male mice were used; For BC model, female mice were used). *p<0.05 100 mg/kg Can vs. vehicle control.

DETAILED DESCRIPTION

Definitions

Figure 1A:
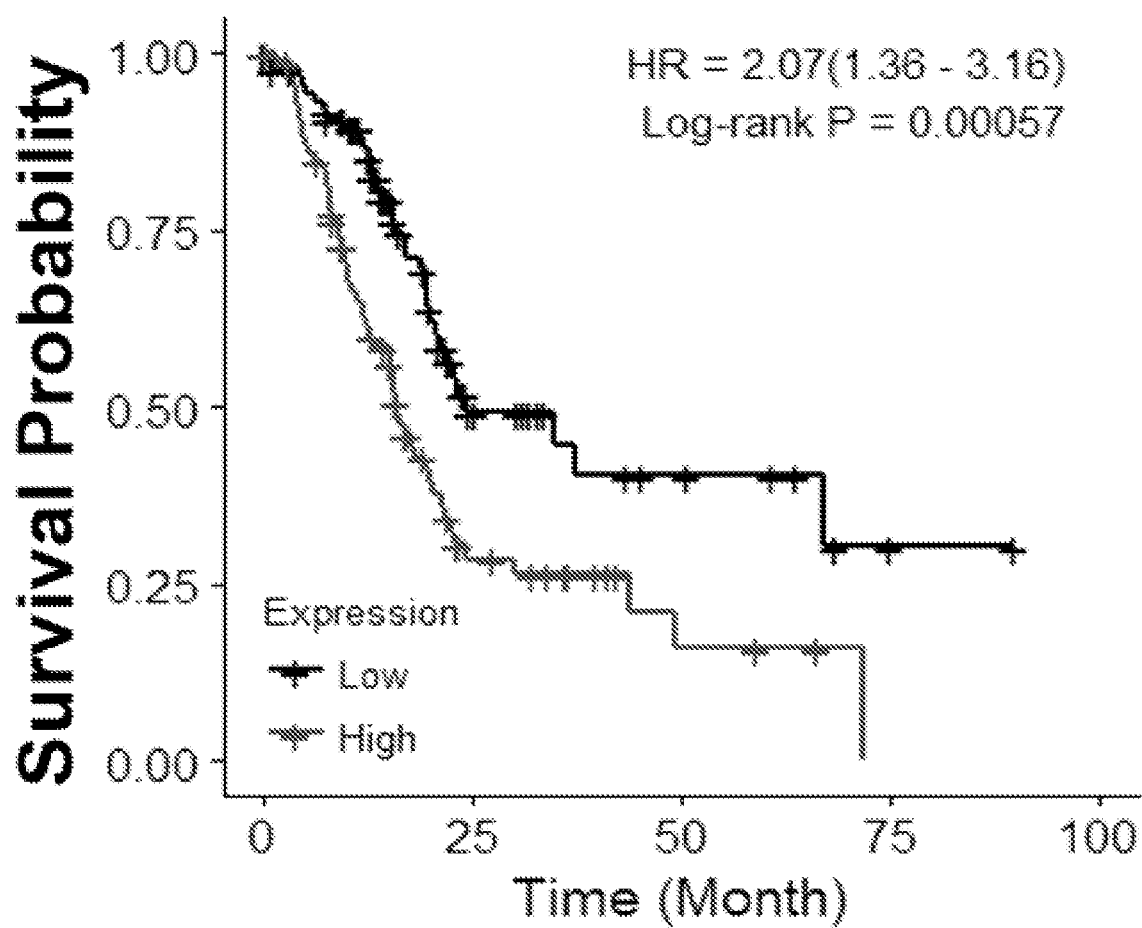
FIGS. 1A-1C show Kaplan-Meier curves in pancreatic ductal adenocarcinoma (PDAC.

In describing and claiming the present disclosure, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

As used herein the term "solid support" relates to a solvent insoluble substrate that is capable of forming linkages (preferably covalent bonds) with soluble molecules. The support is typically formed of polymeric material, such as, without limitation, an acrylamide derivative, glass, plastic, agarose, cellulose, nylon, silica, or magnetized particles. The support can be in particulate form or a monolithic strip or sheet. The surface of such supports may be solid or porous and of any convenient shape.

As used herein, the term "treating" includes prophylaxis of the specific disorder or condition, or alleviation of the symptoms associated with a specific disorder or condition and/or preventing or eliminating said symptoms.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels. An inhibitor is a compound or agent that causes an inhibitory effect on a target moiety, condition or phenotype.

As used herein an "effective" amount or a "therapeutically effective amount" refers to an alteration in the concentration of compound in a patient to provide a desired effect. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein, the term "purified" and like terms relate to the isolation of a molecule or compound in a form that is substantially free of contaminants normally associated with the molecule or compound in a native or natural environment.

As used herein the term "patient" without further designation is intended to encompass any warm blooded vertebrate domesticated animal (including for example, but not limited to livestock, horses, mice, cats, dogs and other pets) and humans receiving a therapeutic treatment, whether or not under the supervision of a physician.

Each of the terms "about" and "approximately," as used herein, mean greater or lesser than the value or range of values stated by 10 percent, but is not intended to designate any value or range of values to only this broader definition. Each value or range of values preceded by the term "about" or the term "approximately" also is intended to encompass the embodiment of the stated absolute value or range of values.

As used herein, "administration" generally means prescription or provision of a pharmaceutical composition to a patient for self-administration by the patient, and may also mean direct administration of a pharmaceutical composition to a patient by a clinician.

EMBODIMENTS

In accordance with one embodiment a method is provided for identifying inhibitors of protein arginine methyltransferase (PRMT), such as protein arginine methyltransferase 5 (PRMT5), and the use of such inhibitors to treat an arginine methyltransferase—mediated disease. The method of treatment comprises contacting arginine methyltransferase with an effective amount of a compound selected from the group consisting of cloperastine hydrochloride, candesartan cilexetil and combinations thereof.

Through the use of an assay that quantifies arginine methyltransferase activity, applicant was able to identify inhibitors of such compounds which have utility an anticancer therapeutics. One assay used to identify arginine methyltransferase inhibitors is described in Example 1.

In accordance with one embodiment an assay for identifying compounds that inhibit PRMT5 methyltransferase activity is provided. In one embodiment the system comprises a PRMT5 substrate, that has been modified by the covalent linkage of a biotin molecule, optionally at the N-terminus of the PRMT5 substrate, a methyl donor, optionally S-adenosyl-1-methionine (SAM), a solid substrate acceptor and a solid substrate donor. In one embodiment the PRMT5 substrate is a protein such as histone H4 peptide that is unmethylated at the arginine (R) located at position 3 (unmeH4R3). The solid substrate donor component of the system comprises covalently linked streptavidin tag and a donor fluorophore or donor photoreactive element capable of producing a signal upon excitation at 680 nm. The solid substrate acceptor component of the system comprises covalently linked ligand that specifically binds to the PRMT5 substrate when the substrate is in its methylated form and a donor fluorophore or donor photoreactive element capable of producing a signal when stimulated by the signal produced by the donor fluorophore or donor photoreactive element. The signal produced by the solid substrate acceptor is dependent on its proximity to the signal producing solid substrate donor substrate such that the solid substrate acceptor will only effectively emit a signal when the solid substrate acceptor and the solid substrate donor are brought into proximity by the binding of the ligand to the methylated PRMT5 substrate, thus allowing for quantifying PRMT5 methyltransferase activity under different conditions.

Figure 2:
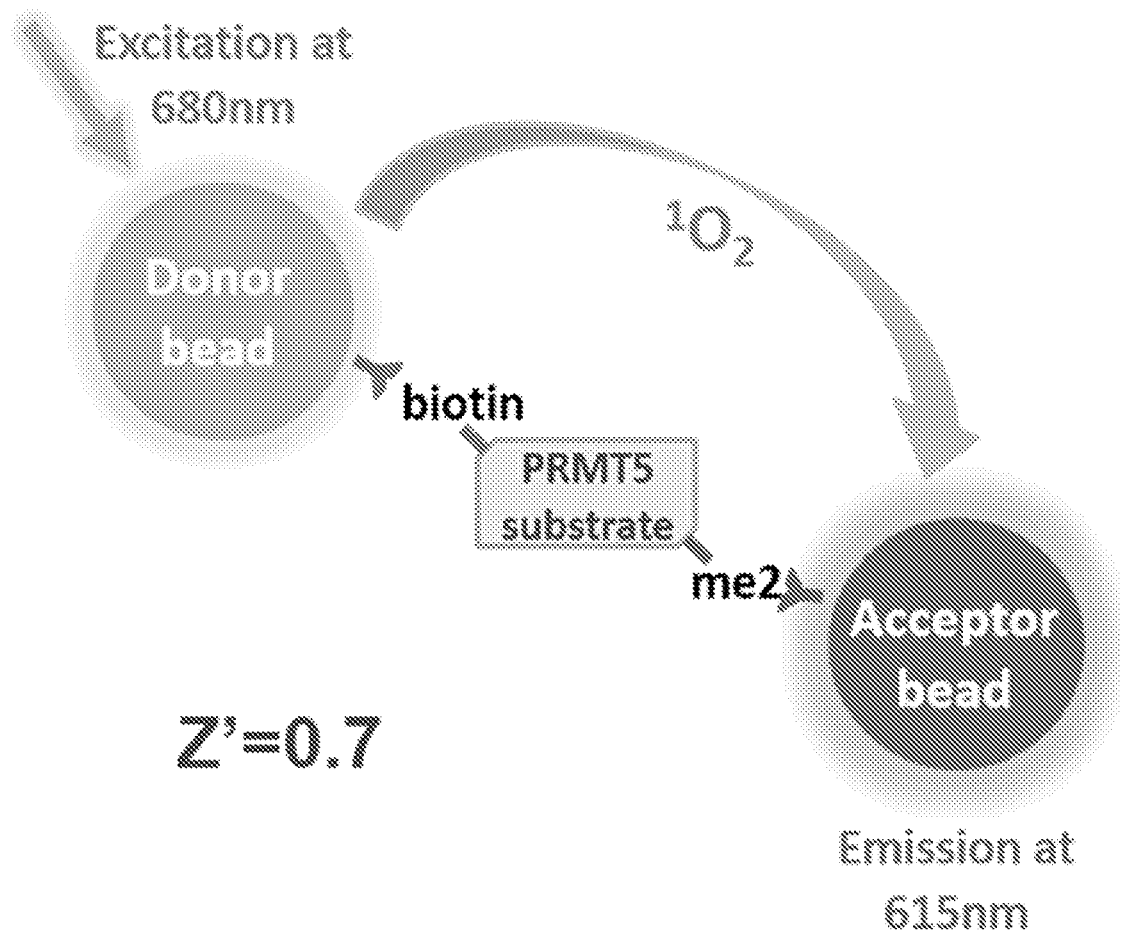
FIG. 2 shows the development of assay-linked immunosorbent assay (AlphaLISA)—high-throughput screen (HTS) used to identify specific PRMT5 inhibitors, Cloperastine (Clo) and Candesartan (Can).
Figure 3A:
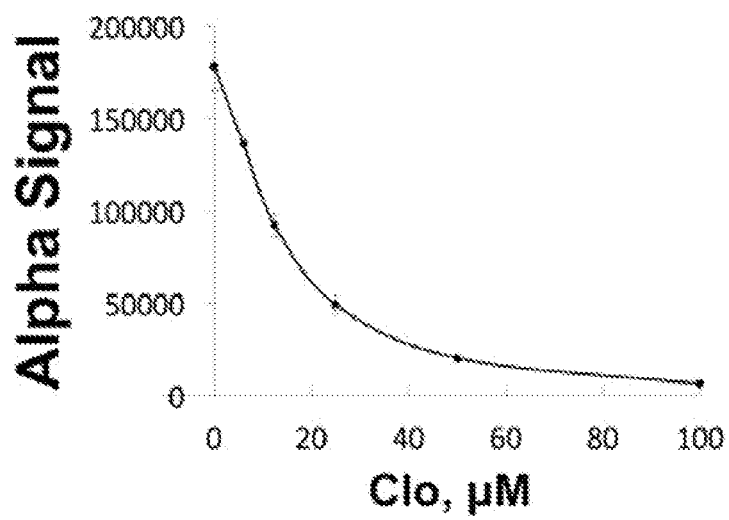
FIGS. 3A-3C are graphs presenting data, produced from the AlphaLISA assay described in Example 1, that shows a concentration-dependent decrease in Alpha signal for Clo (shown in FIG. 3A) and Can (shown in FIG. 3B).
Figure 3B:
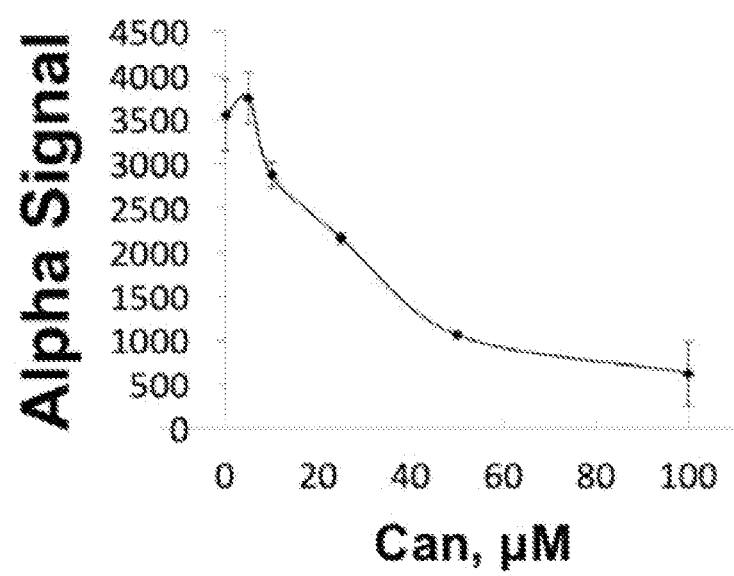
Figures 3C, 4A:
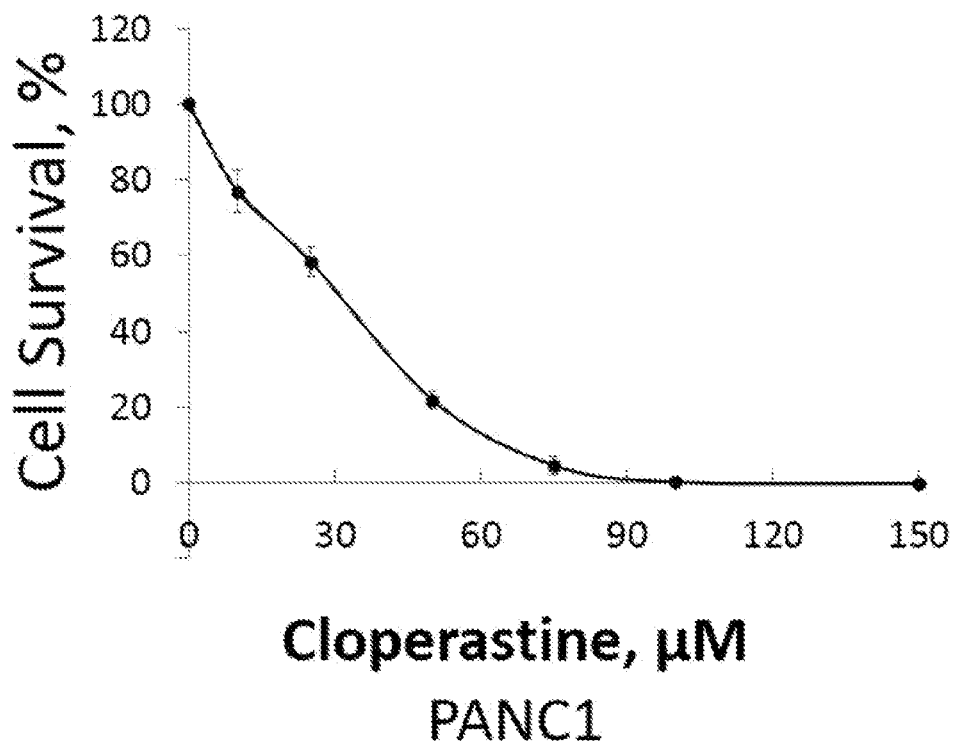
FIGS. 4A-4Q illustrate the results of an MTT [(3-(4,5-dimethylthiazolyl-2)-2,5-diphenyltetrazolium bromide)] assay showing that increasing concentrations of Clo and Can inhibit cell viability in PDAC cells, CRC cells and BC cells. Data is presented for the effect of Clo on PDAC cells including PANC1 (FIG. 4A), MiaPaCa2.

In accordance with one embodiment the system for quantitating PRMT5 enzymatic activity is placed in contact with PRMT5 in the presence or absence of a test compound to see if the test compound inhibits PRMT5's ability to methylate the PRMT5 substrate. FIG. 2 illustrates the experimental approach of employing such a system to identify PRMT5 inhibitors. Using such a system (AlphaLISA HTS) to identify two FDA-approved drugs, Cloperastine hydrochloride (Clo) and Candesartan cilexetil (Can) as inhibitors of PRMT5 methylase activity. In SAM-bound conditions, Clo bound to a site distinct from SAM on PRMT5. In apo PRMT5 condition, several binding residues for Clo overlapped with SAM, suggesting that Clo could block PRMT5 activity by interfering with binding similar residues as SAM. Similar observations were seen for the Can-PRMT5 interaction in the presence and absence of SAM respectively. The $IC_{50}$ binding affinities of Clo and Can were 27 uM and 33 uM by AlphaLISA assay, respectively (FIG. 3C). Clo showed favorable binding energies under both the presence and absence of SAM, Can showed more binding affinity in the Apo-PRMT5 condition (−6.215 kcal/mol). Ligand affinity map highlighting PRMT5 residues involved in the SAM-bound condition and apo condition for Clo and Can reveal the PRMT5 residues such as E444 (part of catalytic cleft) and F327 (critical for substrate binding) are important in both docking conditions for Clo and Can. Both drugs can be use in new indications via their ability to inhibit PRMT5 in PDAC, CRC and BC cells and in turn, inhibit the activation of its critical substrate, NF-κB, a known tumor promoter. This effect is anticipated to lead to a decrease in the tumor phenotype, thereby highlighting the use of Clo and Can to be repurposed for new indications in cancer patients.

In accordance with one embodiment methods are provided for inhibiting a protein arginine methyltransferase (PRMT) by contacting the arginine methyltransferase with an effective amount of a compound selected from the group consisting of cloperastine hydrochloride, candesartan cilexetil or a combination of cloperastine hydrochloride and candesartan. The present disclosure also encompasses analogs and derivatives of cloperastine hydrochloride and candesartan cilexetil that have been modified but retain their inhibitory effect on arginine methyltransferases such as protein arginine methyltransferase 5 (PRMT5). Such modification include the attachment of functional groups that enhance solubility or retention in the bloodstream without impacting the ability of the modified compound to interact with PRMT5.

In accordance with one embodiment a method of inhibiting a protein arginine methyltransferase (PRMT) is provided. The inhibition of the PRMT5 can be conducted in vitro or in vivo. In one embodiment the method comprising the step of contacting the protein arginine methyltransferase with a compound selected from the group consisting of cloperastine hydrochloride, candesartan cilexetil or a protein arginine methyltransferase inhibiting analogs of cloperastine hydrochloride, candesartan cilexetil, or any combination of such compounds. In one embodiment the arginine methyltransferase is PRMT5, and optionally PRMT5 activity is inhibited by contact with cloperastine hydrochloride and/or candesartan cilexetil. In one embodiment the arginine methyltransferase, optionally PRMT5, is contacted with both cloperastine hydrochloride and candesartan cilexetil either sequentially or simultaneously.

In accordance with one embodiment the activity of PRMT5 is inhibited within a cell, wherein the cell is contacted with a compound selected from the group consisting of cloperastine hydrochloride, candesartan cilexetil or an arginine methyltransferase inhibiting analogs of cloperastine hydrochloride, candesartan cilexetil, or any combination of such compounds. In one embodiment the cell is contacted with a composition comprising cloperastine hydrochloride and/or candesartan cilexetil. In one embodiment the cells contacted are cells of a patient. The cells of a patient can be contacted locally, by injection of a composition comprising an arginine methyltransferase inhibitor, or the cells can be contacted via a systemic administration of a composition comprising a protein arginine methyltransferase inhibitor.

In accordance with one embodiment a subject is administered a pharmaceutical composition comprising a compound selected from the group consisting of cloperastine hydrochloride, candesartan cilexetil and protein arginine methyltransferase inhibiting analogs of cloperastine hydrochloride and/or candesartan cilexetil, or a composition comprising any combination of such compounds. In one embodiment the administered pharmaceutical composition comprises a compound selected from the group consisting of cloperastine hydrochloride and candesartan cilexetil, and in one embodiment the composition comprises cloperastine hydrochloride and candesartan cilexetil.

In one embodiment a pharmaceutical composition is provided comprising cloperastine hydrochloride and/or candesartan cilexetil and a pharmaceutical acceptable carrier. In one embodiment the pharmaceutical composition further comprises an antitumor agent, including for example a chemotherapeutic agent or immunotherapeutic agent. In one embodiment the chemotherapeutic agent is selected from an alkylating agent, an antimetabolite, a topoisomerase inhibitor and a mitotic inhibitor.

In one embodiment the pharmaceutical composition comprises cloperastine hydrochloride and/or candesartan cilexetil, a pharmaceutical acceptable carrier and
i) an alkylating agent selected from the group consisting of Busulfan (MYLERAN®), Cyclophosphamide and Temozolomide (TEMODAR®); or
ii) an antimetabolite selected from the group consisting of 5-fluorouracil (5-FU), 6-mercaptopurine (6-MP), Capecitabine (Xeloda), and Gemcitabine; or
iii) an anti-tumor antibiotic selected from the group consisting of Dactinomycin (COSMEGEN®), Bleomycin, Daunorubicin (CERUBIDINE®, or RUBIDOMYCIN®), and Doxorubicin (ADRIAMY-CIN PFS®, or ADRIAMYCIN RDF®);

iv) a topoisomerase inhibitor selected from the group consisting of Etoposide, Irinotecan (CAMPTOSAR®) and Topotecan (HYCAMTIN®);

v) a mitotic inhibitor selected from the group consisting of Docetaxel (TAXOTERE®), Eribulin (HALAVEN®), Ixabepilone (IXEMPRA®), Paclitaxel (TAXOL®) and Vinblastine; or vi) any combination of i) through v).

In one embodiment the pharmaceutical composition comprises cloperastine hydrochloride and/or candesartan cilexetil, a pharmaceutical acceptable carrier and an immune checkpoint inhibitor, including for example, a PD-1 inhibitor, such as Pembrolizumab (KEYTRUDA®) or a PD-L1 inhibitor such as Atezolizumab (TECENTRIQ®).

Additional antitumor agents suitable for use in combination with the protein arginine methyltransferase inhibitors of the present disclosure include: Albumin-bound paclitaxel (nab-paclitaxel or ABRAXANE®), Capecitabine (XELODA®), Eribulin (HALAVEN®), Gemcitabine (GEMZAR®), Ixabepilone (IXEMPRA®), Liposomal doxorubicin (DOXIL®), Mitoxantrone, Platinum (CARBOPLATIN®, CISPLATIN®), and Vinorelbine (NAVELBINE®) as well as any combinations thereof.

In one embodiment a pharmaceutical composition is provided comprising cloperastine hydrochloride and/or candesartan cilexetil, a pharmaceutical acceptable carrier and one of the following combinations of antitumor agents:

AC: Adriamycin and Cytoxan;
AT: Adriamycin and Taxotere;
CMF: Cytoxan, methotrexate, and fluorouracil;
FAC: Fluorouracil, Adriamycin, and Cytoxan; or
CAF: Cytoxan, Adriamycin, and fluorouracil. In one embodiment such a pharmaceutical composition is used to treat breast cancer.

In one embodiment a pharmaceutical composition is provided comprising cloperastine hydrochloride and/or candesartan cilexetil, a pharmaceutical acceptable carrier and an antitumor agent selected from the group consisting of 5-Fluorouracil (5-FU®), Capecitabine (XELODA®), Irinotecan (CAMPTOSAR®), Oxaliplatin (ELOXATIN®), Trifluridine, tipiracil and (LONSURF®); a combination drug in pill form comprising Trifluridine and tipiracil). In one embodiment such a pharmaceutical composition is used to treat pancreatic cancer.

In one embodiment a pharmaceutical composition is provided comprising cloperastine hydrochloride and/or candesartan cilexetil, a pharmaceutical acceptable carrier and an antitumor agent selected from the group consisting of Bevacizumab (AVASTIN®), Irinotecan Hydrochloride (CAMPTOSAR®), Capecitabine (XELODA®), Cetuximab, Ramucirumab (CYRAMZA®), Oxaliplatin (ELOXATIN®), Cetuximab (ERBITUX®), Fluorouracil, Ipilimumab (YERVOY®), Pembrolizumab (KEYTRUDA®), Leucovorin Calcium, LONSURF (Trifluridine and Tipiracil Hydrochloride®), Nivolumab (OPDIVO®), Oxaliplatin, Panitumumab (VECTIBIX®), Regorafenib (STIVARGA®), Ziv-Aflibercept (ZALTRAP®), and Bevacizumab (ZIRABEV®). In one embodiment such a pharmaceutical composition is used to treat colon cancer. The protein arginine methyltransferase inhibitory compounds can be administered to subjects using any standard route of administration, including parenterally (such as intravenously, intraperitoneally, subcutaneously or intramuscularly), intrathecally, transdermally, rectally, orally, nasally or by inhalation. In exemplary embodiments, pharmaceutical compositions may comprise buffering agents to achieve a physiological compatible pH. The buffering agents may include any compounds capable of buffering at the desired pH such as, for example, phosphate buffers (e.g., PBS), triethanolamine, Tris, bicine, TAPS, tricine, HEPES, TES, MOPS, PIPES, cacodylate, MES, acetate, citrate, succinate, histidine or other pharmaceutically acceptable buffers.

In accordance with one embodiment a subject is administered a pharmaceutical composition comprising cloperastine hydrochloride and a pharmaceutical composition comprising candesartan cilexetil, wherein there is a temporal delay between administering the cloperastine hydrochloride and candesartan cilexetil pharmaceutical compositions. The delay may be any length of time designed to maximize the inhibitory effect. In one embodiment the delay between administering the candesartan cilexetil and cloperastine hydrochloride compounds can be minutes, hours, days, weeks or months. In one embodiment the temporal delay is selected from 1 hour, 12 hours, 24 hours, 2 days, 3 days, 4 days, 5 days, 6 days, 1 week, 2 weeks and 1 month.

In accordance with one embodiment a pharmaceutical composition is provided for use in inhibiting the methylase activity of PRMT5, wherein the composition comprises both cloperastine hydrochloride and candesartan cilexetil as active agents and a pharmaceutical acceptable carrier. In one embodiment the composition is used to treat cancer, including a cancer selected from the group consisting of pancreatic ductal adenocarcinoma (PDAC), colorectal cancer (CRC) and breast cancer (BC). In one embodiment a pharmaceutical composition comprising cloperastine hydrochloride and/or candesartan cilexetil further comprises an antineoplastic agent, including for example chemotherapeutic agents, immunotherapeutic agents, alkylating agents, plant alkaloids, antimetabolites, anthracyclines, topoisomerase inhibitors, DNA methyltransferase (DNMT) inhibitors, other epigenetic enzyme inhibitors, such as histone deacetylase (HDAC) inhibitors, targeted therapy drugs, such as trastuzmab, protein kinase inhibitors, such as Imatimib (GLEEVEC®), and the composition is used to treat cancer, including a cancer selected from the group consisting of pancreatic ductal adenocarcinoma (PDAC), colorectal cancer (CRC) and all subtypes (TNBC, or estrogen receptor positive et al) of breast cancer (BC). In one embodiment the pharmaceutical composition comprises cloperastine hydrochloride, and/or candesartan cilexetil, and an antitumor agent and a pharmaceutical acceptable carrier. In one embodiment the antitumor agent is a chemotherapeutic agent.

PRMTs are enzymes that catalyze the transfer of methyl groups from S-Adenosyl-L-Methionine (SAM) to specific arginine residues of proteins. Elevated activity of PRMT5 has been described in the art for multiple disorders, including various types of cancer. While not wishing to be bound by any particular theory, it is believed that inhibition of PRMT5 causes a decrease in the activation of nuclear factor κB (NF-κB) leading to a decrease in tumor progression.

In accordance with one embodiment a method of treating a protein arginine methyl transferase-mediated disorder is provided wherein the method comprises administering to a subject in need thereof a therapeutically effective amount of cloperastine hydrochloride, candesartan cilexetil or combinations thereof. In one embodiment the arginine methyl transferase-mediated disorder is associated with excessive PRMT5 activity. In one embodiment the protein arginine methyl transferase-mediated disorder is a cancer.

The type of cancer is not particularly limited. In certain embodiments the cancer is characterized as a cancer that has increased activity of PRMT5 compared to a non-cancer sample of the same tissue type. The identification of a cancer that has increased activity of PRMT5 can be readily identified by a person of ordinary skill in the art using routine methods (e.g., Western blot, Elisa, or PCR), including the methods described herein. In another embodiment the cancer is characterized as a cancer that has increased activation of NF-κB compared to a non-cancer sample of the same tissue type. The identification of a cancer that has increased activity of NF-κB can be readily identified by a person of ordinary skill in the art using routine methods (e.g., Western blot, Elisa, or PCR). In a further embodiment of the invention the cancer has increased activity of PRMT5 and increased activity of NF-κB. Examples of treatable cancers with PRMT5 inhibitors include cancers of the head and neck, eye, skin, mouth, throat, esophagus, chest, bone, lung, colon, sigmoid, rectum, stomach, prostate, breast, ovaries, kidney, liver, pancreas, brain, intestine, heart, or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-borne tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, chronic lymphocytic leukemia, hairy cell leukemia, or multiple myeloma. In some aspects, the cancer is a solid tumor. In accordance with an embodiment, the cancer is selected from gastrointestinal cancer, skin cancer, lung cancer, brain cancer, ovarian cancer, prostate cancer, lymphoma, melanoma, and breast cancer.

In one embodiment the cancer to be treated by the administration of a protein arginine methyl transferase inhibitor is selected from the group consisting of pancreatic ductal adenocarcinoma (PDAC), colorectal cancer (CRC) and all subtypes of breast cancer (BC). In another embodiment, the cancer to be treated is pancreatic cancer, or colorectal cancer.

PRMT5 activity has been shown to be increased in a variety of diseases other than cancer, and inhibition of PRMT5 has been described in the art as a viable treatment of multiple diseases, including autoimmune diseases, inflammatory disease, metabolic disorders, neurological and neurodegenerative disorders, cardiovascular disorders, and blood disorders. Suitable diseases that can be treated through the use of an arginine methyl transferase inhibitor in accordance with the present disclosure include, for example, autoimmune diseases, inflammatory disease, metabolic disorders, neurological and neurodegenerative disorders, cardiovascular diseases, and blood disorders.

Examples of autoimmune diseases treatable through the use of an arginine methyl transferase inhibitor in accordance with the present disclosure include alopecia areata, autoimmune hemolytic anemia, autoimmune hepatitis, dermatomyositis, diabetes (type 1), juvenile idiopathic arthritis, glomerulonephritis, Graves' disease, Guillain-Barré syndrome, idiopathic thrombocytopenic purpura, myasthenia gravis, myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, thyroiditis, uveitis, vitiligo, and granulomatosis with polyangiitis (Wegener's).

Examples of inflammatory diseases treatable through the use of an arginine methyl transferase inhibitor in accordance with the present disclosure include ankylosing spondylitis, arthritis (e.g., osteoarthritis, rheumatoid arthritis (RA), psoriatic arthritis), gout, eczema, gastritis, splenitis, sinusitis, hepatitis, nephritis, psoriasis, vasculitis, atherosclerosis, sarcoidosis, pleurisy, asthma, atherosclerosis, Crohn's disease, colitis, dermatitis, diverticulitis, fibromyalgia, hepatitis, irritable bowel syndrome (IBS), systemic lupus erythematous (SLE), nephritis, and ulcerative colitis.

Examples of metabolic disorders treatable through the use of an arginine methyl transferase inhibitor in accordance with the present disclosure include diabetes (type 1 and type 2), phenylketonuira, and obesity.

Examples of neurological and neurodegenerative disorders treatable through the use of an arginine methyl transferase inhibitor in accordance with the present disclosure include drug abuse (e.g., methamphetamine addiction), Alzheimer's disease, amyotrophic lateral sclerosis, Angelman syndrome, Asperger syndrome, autism, bipolar disorder, cerebral arteriosclerosis, Charcot-Marie-Tooth disease, chronic pain, Cushing's syndrome, Creutzfeldt-Jakob disease, dementia, Huntington's disease, inclusion body myositis, Parkinson's disease, and Reye syndrome. Examples of cardiovascular disorders treatable with the inventive method include coronary artery disease, angina, myocardial infarction, stroke, hypertensive heart disease, rheumatic heart disease, cardiomyopathy, arrhythmia, congenital heart disease, valvular heart disease, carditis, aortic aneurysms, peripheral artery disease, and venous thrombosis.

Examples of blood disorders treatable through the use of an arginine methyl transferase inhibitor in accordance with the present disclosure include anemia, bleeding disorders, hemophilia, sickle cell anemia, hemoglobinopathy, β-thalassemia, and blood clots.

In accordance with embodiment 1 a method of inhibiting a protein arginine methyltransferase (PRMT) is provided. The method comprises the step of contacting the arginine methyltransferase with a compound selected from the group consisting of cloperastine hydrochloride, candesartan cilexetil and arginine methyltransferase inhibiting analogs of cloperastine hydrochloride and candesartan cilexetil.

In accordance with embodiment 2 the protein arginine methyltransferase of embodiment 1 is contacted with both cloperastine hydrochloride and candesartan cilexetil.

In accordance with embodiment 3 the method of embodiment 1 or 2 is conducted wherein the protein arginine methyltransferase is contacted with a composition comprising cloperastine hydrochloride and candesartan cilexetil.

In accordance with embodiment 4 the method of any one of embodiments 1-3 is conducted wherein said protein arginine methyltransferase is first contacted with cloperastine hydrochloride or candesartan cilexetil and then subsequently contacted with the alternative compound not used in the first contact.

In accordance with embodiment 5 the method of any one of embodiments 1-4 is conducted wherein said contact takes place in a cell.

In accordance with embodiment 6 the method of any one of embodiments 1-5 is conducted wherein a patient is administered a pharmaceutical composition comprising a compound selected from the group consisting of cloperastine hydrochloride, candesartan cilexetil and arginine methyltransferase inhibiting analogs of cloperastine hydrochloride and candesartan cilexetil and a pharmaceutically acceptable carrier.

In accordance with embodiment 7 the method of any one of embodiments 1-7 is conducted wherein a patient is administered a pharmaceutical composition comprising cloperastine hydrochloride and a pharmaceutical composition comprising candesartan cilexetil, wherein there is a temporal delay between administering the cloperastine hydrochloride and candesartan cilexetil pharmaceutical compositions.

In accordance with embodiment 8 the method of embodiments 7 is conducted wherein the temporal delay is selected from 1 hour, 12 hours, 24 hours, 2 days, 3 days, 4 days, 5 days, 6 days, 1 week, 2 weeks and 1 month.

In accordance with embodiment 9 the method of any one of embodiments 1-6 is conducted wherein a patient is administered a pharmaceutical composition comprising cloperastine hydrochloride and candesartan cilexetil.

In accordance with embodiment 10 the method of any one of embodiments 1-6 is conducted wherein a patient is administered a pharmaceutical composition in accordance with any one of embodiments 12-21.

In accordance with embodiment 11 the method of any one of embodiments 1-10 is conducted wherein the arginine methyl transferase is protein arginine methyltransferase 5 (PRMT5).

In accordance with embodiment 12 a pharmaceutical composition is provided comprising cloperastine hydrochloride, candesartan cilexetil and a pharmaceutical acceptable carrier.

In accordance with embodiment 13 a pharmaceutical composition of embodiment 12 is provided wherein the composition further comprises an antitumor agent.

In accordance with embodiment 14 a pharmaceutical composition of embodiment 12 or 13 is provided wherein the antitumor agent is selected from the group consisting of Cyclophosphamide, Temozolomide, 5-fluorouracil (5-FU), 6-mercaptopurine (6-MP), Capecitabine, Gemcitabine, Dactinomycin, Bleomycin, Daunorubicin, Doxorubicin, Etoposide, Irinotecan, Topotecan, Docetaxel, Eribulin, Ixabepilone, Paclitaxel, Vinblastine, Albumin-bound paclitaxel (nab-paclitaxel), Eribulin, Liposomal doxorubicin, Mitoxantrone, Platinum, Vinorelbine, Oxaliplatin, Trifluridine, tipiracil, Bevacizumab, Irinotecan Hydrochloride, Cetuximab, Ramucirumab, Ipilimumab, Pembrolizumab, Leucovorin Calcium, Nivolumab, Panitumumab, Regorafenib, and Ziv-Aflibercept, or any combination thereof.

In accordance with embodiment 15 a pharmaceutical composition of any one of embodiments 12-14 is provided wherein the pharmaceutical composition further comprises an immune checkpoint inhibitor, optionally wherein the checkpoint inhibitor is a PD-1 inhibitor, such as Pembrolizumab or a PD-L1 inhibitor such as Atezolizumab as well as any combinations thereof.

In accordance with embodiment 15.5 a pharmaceutical composition of any one of embodiments 12-15 is provided wherein the composition comprises an HDAC inhibitor, a DNMT (DNA methylase inhibitors), optionally wherein the DNMT is 5-aza, a proteasome inhibitor, optionally wherein the proteasome inhibitor is PS-341 (Bortizomib), or Imatinib (Gleevec), optionally wherein the pharmaceutical composition comprises cloperastine hydrochloride and/or candesartan cilexetil and a DNMT inhibitor and/or HDAC inhibitor, optionally wherein the pharmaceutical composition comprises cloperastine hydrochloride and/or candesartan cilexetil and 5-aza.

In accordance with embodiment 16 a pharmaceutical composition of any one of embodiments 12-15 is provided wherein the composition comprises a combination of antitumor agents selected from the following combinations:
    AC: Adriamycin and Cytoxan;
    AT: Adriamycin and Taxotere;
    CMF: Cytoxan, methotrexate, and fluorouracil;
    FAC: Fluorouracil, Adriamycin, and Cytoxan; or
    CAF: Cytoxan, Adriamycin, and fluorouracil.

In accordance with embodiment 17 a pharmaceutical composition of any one of embodiments 12-16 is provided wherein the pharmaceutical composition comprises cloperastine hydrochloride and/or candesartan cilexetil, a pharmaceutical acceptable carrier and an antitumor agent selected from the group consisting of 5-Fluorouracil (5-FU®), Capecitabine (XELODA®), Irinotecan (CAMPTOSAR®), Oxaliplatin (ELOXATIN®), Trifluridine, tipiracil and LONSURF®, a combination drug in pill form comprising Trifluridine and tipiracil), optionally wherein such pharmaceutical composition is used to treat pancreatic cancer.

In accordance with embodiment 18 a pharmaceutical composition of any one of embodiments 12-16 is provided wherein the pharmaceutical composition comprises cloperastine hydrochloride and/or candesartan cilexetil, a pharmaceutical acceptable carrier and an antitumor agent selected from the group consisting of Bevacizumab (AVASTIN®), Irinotecan Hydrochloride (CAMPTOSAR®), Capecitabine (XELODA®), Cetuximab, Ramucirumab (CYRAMZA®), Oxaliplatin (ELOXATIN®), Cetuximab (ERBITUX®), Fluorouracil, Ipilimumab (YERVOY®), Pembrolizumab (KEYTRUDA®), Leucovorin Calcium, LONSURF (Trifluridine and Tipiracil Hydrochloride®), Nivolumab (OPDIVO®), Oxaliplatin, Panitumumab (VECTIBIX®), Regorafenib (STIVARGA®), Ziv-Aflibercept (ZALTRAP®), and Bevacizumab (ZIRABEV®), or any combination thereof, optionally wherein the pharmaceutical composition is used to treat colon cancer.

In accordance with embodiment 19 a pharmaceutical composition of any one of embodiments 12-16 is provided wherein the pharmaceutical composition comprises cloperastine hydrochloride and/or candesartan cilexetil, a pharmaceutical acceptable carrier and
    i) an alkylating agent selected from the group consisting of Busulfan (MYLERAN®), Cyclophosphamide and Temozolomide (TEMODAR®); or
    ii) an antimetabolite selected from the group consisting of 5-fluorouracil (5-FU), 6-mercaptopurine (6-MP), Capecitabine (Xeloda), and Gemcitabine; or
    iii) an anti-tumor antibiotic selected from the group consisting of Dactinomycin (COSMEGEN®), Bleomycin, Daunorubicin (CERUBIDINE®, or RUBIDOMYCIN®), and Doxorubicin (ADRIAMYCIN PFS®, or ADRIAMYCIN RDF®);

iv) a topoisomerase inhibitor selected from the group consisting of Etoposide, Irinotecan (CAMPTOSAR®) and Topotecan (HYCAMTIN®);

v) a mitotic inhibitor selected from the group consisting of Docetaxel (TAXOTERE®), Eribulin (HALAVEN®), Ixabepilone (IXEMPRA®), Paclitaxel (TAXOL®) and Vinblastine; or vi) any combination of i) through v), optionally wherein said composition is used to treat breast cancer.

In accordance with embodiment 20 a pharmaceutical composition of any one of embodiments 12-19 is provided wherein the pharmaceutical composition comprises an immune checkpoint inhibitor, including for example, a PD-1 inhibitor, such as Pembrolizumab (KEYTRUDA®) or a PD-L1 inhibitor such as Atezolizumab (TECENTRIQ®).

In accordance with embodiment 21 a pharmaceutical composition of any one of embodiments 12-16 is provided wherein the pharmaceutical composition comprises a chemotherapeutic agent.

In accordance with embodiment 22 a method of treating an arginine methyl transferase-mediated disorder is provided wherein the method comprises the step of administering to a subject in need thereof a therapeutically effective amount of a compound selected from the group consisting of cloperastine hydrochloride, candesartan cilexetil and combinations thereof.

In accordance with embodiment 23 a method of embodiment 22 is provided wherein the arginine methyl transferase-mediated disorder is associated with excessive PRMT5 activity.

In accordance with embodiment 24 a method of embodiment 22 or 23 is provided wherein the arginine methyl transferase-mediated disorder is a cancer wherein the cancer is characterized as a cancer that has increased activity of PRMT5 compared to a non-cancer sample of the same tissue type, or the cancer is characterized as a cancer that has increased activation of NF-κB compared to a non-cancer sample of the same tissue type.

In accordance with embodiment 25 a method of any one of embodiments 22-24 is provided wherein the cancer is selected from the group consisting of pancreatic ductal adenocarcinoma (PDAC), colorectal cancer (CRC) and breast cancer (BC).

In accordance with embodiment 26 a method of any one of embodiments 22-24 is provided wherein the cancer is pancreatic ductal adenocarcinoma (PDAC.

In accordance with embodiment 27 a method of any one of embodiments 22-24 is provided wherein the cancer is colorectal cancer (CRC).

In accordance with embodiment 28 a method of any one of embodiments 22-24 is provided wherein the cancer is breast cancer, optionally triple negative breast cancer (TNBC) and estrogen receptor positive (ER+) breast cancer (BC).

In accordance with embodiment 29 a pharmaceutical composition of any one of claims 11-13 is provided for use in treating a protein arginine methyl transferase-mediated disorder.

In accordance with embodiment 30 the pharmaceutical composition is used wherein the arginine methyl transferase-mediated disorder is cancer.

In accordance with embodiment 30 the pharmaceutical composition is used wherein the cancer is selected from the group consisting of pancreatic ductal adenocarcinoma (PDAC), colorectal cancer (CRC) and any subtypes of breast cancer (BC).

EXAMPLE 1

Assay for Detecting Protein Arginine Methyl Transferase Inhibitors Cell Lines and Reagents.

PDAC (PANC1, MiaPaCa2 and AsPC1) and BC (MDA-MB-231, BT20, and MCF-7) cell lines were kind gifts from Dr. Murray Korc and Dr. Britney Shea-Herbert respectively at Indiana University School of Medicine (IUSM). The CRC cell lines (HT29, HCT116, and DLD1) cell lines were obtained from American Type Culture Collection (Manassas, VA). Cell lines were authenticated using 9 Marker STR Profile (IDEXX Bioresearch, Columbia, MO). PDAC (except AsPC1) and BC cell lines (MDA-MB-231, BT20, and MCF7) were cultured in Dulbecco's Modified Eagle Medium (DMEM) (GE Healthcare, Chicago, IL), supplemented with 1% of penicillin/streptomycin and 5% fetal bovine serum (FBS) (Thermo Fisher Scientific, Waltham, MA). CRC cells and AsPC1 were grown in Roswell Park Memorial Institute Medium (RPMI) 1640 (GE Healthcare), with 1% penicillin/streptomycin and 5% FBS. All cell lines were used within passage 6. Cell lines were maintained in a sterile incubator at 37° C. under 5% $CO_2$.

For AlphaLISA HTS: the substrate, histone H4 peptide unmethylated at arginine (R) 3 (unmeH4R3) was purchased from AnaSpec (Fremont, CA). The 23-amino acid H4R3 peptide was biotinylated at its N' terminus: SGRGKGGKGLGKGGAKRHRKVLRGG-K(biotin)-$NH_2$ (SEQ ID NO: 1). S-adenosyl methionine (SAM) was used as a methyl group donor (New England Biolabs, Ipswich, MA). Compound libraries comprising of FDA-approved drugs, synthetic and semi-synthetic natural products as well as bioactives were collectively purchased from Analyticon Discovery (Rockville, MD), MilliporeSigma (Burlington, MA) and Microsource Discovery Systems Inc (Gaylordsville, CT). Acceptor beads specific for dimethylated H4R3, Donor beads with a streptavidin tag, assay buffer, OptiPlate™ 384-well white bottom plates, TopSeal™-A film to seal the plates and EnVision® Multilabel Reader were sourced from PerkinElmer (Waltham, MA). Clo and Can were sourced from Sigma-Aldrich (St. Louis, MO), both in powder form and dissolved in appropriate dimethyl sulfoxide (DMSO) stocks for experimental use.

Primary antibodies for symmetric dimethylation at arginine (R) 30 subunit of p65 (detected by generating a customized polyclonal primary antibody in collaboration with GenScript Inc, Piscataway, NJ) and R-actin (Sigma-Aldrich) with their corresponding secondary antibodies were used.

AlphaLISA-Based High Throughput Screening.

A detailed description of optimization of the AlphaLISA HTS screening protocol has already been published previously. 10 μL of substrate:SAM mixture (60 nM unmethylated H4R3 and 200 μM SAM) was added to the respective wells, following which 1 mM DMSO stock of library compounds was pipetted into the wells. Final compound concentration was 12.5 μM, with a final DMSO of 1.25% per well. 10 μl of PRMT5 enzyme, purified using co-immunoprecipitation experiments in 293 cells overexpressing Flag-tagged PRMT5 was then added to the wells, as described earlier. No compound was added to wells with positive controls that denoted "maximal signal" in the reaction. For negative control wells, no enzyme or compound was added which denoted the "background signal". The plates were incubated at R.T. for 1 hour with the substrate:SAM:enzyme mixture, followed by addition of 5 μl Acceptor beads specific for dimethylated H4R3 (1:50 dilution of the 5 mg/ml stock) into all wells of the assay plates and incubated at R.T.

for 1 hour. Finally, 5 µl of Donor beads (1:50 dilution of the 5 mg/ml stock) were added to the plates and incubated at R.T. for 30 minutes. Alpha signal was then quantified using the EnVision® reader.

EXAMPLE 2

Inhibition of Cancer Cells With Protein Arginine Methyl Transferase Inhibitors MTT [(3-(4,5-dimethylthiazolyl-2)-2,5-diphenyltetrazolium bromide)] assay Cells were grown to 60% density in clear flat-bottom 96-well plates (Corning Inc, Corning, NY) for 24 hours and treated with a range of concentrations of either Clo or Can respectively, followed by incubation for 4 days. 10 µl of MTT dye (Sigma-Aldrich) was added to each well and incubated for 2 hours at 37° C. The media:MTT mixture was then removed and 10 µl DMSO was added per well. Absorbance was measured using Synergy H4 Multi-Mode Reader (BioTek Instruments, Winooski, VT).

Three-Dimensional (3D) Colony Formation Assay.

PANC1 and MDA-MB-231 (1000 cells) as well as HT29 (250 cells) were seeded per well within ultra-low attachment plates (Corning Inc) in media comprising 3% Reduced Growth Factor-Matrigel (BD Biosciences, Franklin Lakes, NJ). Clo and Can were added in a concentration range from 5-100 µM and 5-120 µM respectively after seeding for 48 hours. After 72 hours of drug treatment, the cells were stained using 10% Alamar blue dye (Fisher) and fluorescence was quantified using a Synergy H4 Reader.

Western Blotting.

PDAC, CRC and BC cells were pelleted post treatment with either Clo or Can in phosphate buffered saline (PBS). Pellets were lysed by overnight incubation at −80° C. as well as addition of lysis buffer [(10 mM Tris-Cl pH 8.0, 1 mM EDTA, 1% Triton X, 0.1% sodium deoxycholate, 0.1% SDS (sodium dodecyl sulfate), 14 mM NaCl, 1 mM phenylmethylsulfonyl fluoride]. Protein concentration for each sample was determined using Protein Assay Reagent (Biorad, Hercules, CA). Equal protein concentrations were run on a 10% SDS-PAGE (polyacrylamide gel electrophoresis) gel and transferred using polyvinylidene fluoride membrane (Thermo Fisher Scientific). Membranes were exposed to respective primary and secondary antibodies at dilutions and times based on manufacturer's instructions. Protein signal was detected using enhanced chemiluminescence (ECL) reagent (PerkinElmer).

NF-κB Luciferase Assay.

The NF-κB luciferase lentiviral construct pLA-NFκBmCMV-luc-H4-puro (containing five tandem copies of the NF-κB site from the IP10 gene) was introduced in the respective cell lines using Lipofectamine™ LTX Reagent and PLUS Reagents (Thermo Fisher Scientific). Luciferase activity was measured after 48 hours (with or without drug treatment) using Reporter Lysis Buffer kit (Promega, Madison, WI) as per manufacturer's instructions and the Synergy H4 Reader.

Quantitative reverse-transcriptase polymerase chain reaction (qRT-PCR).

Following treatment with either Clo or Can for 48 hours, total RNA was isolated from the respective cell lines using Trizol as described earlier. First strand complementary DNA was generated using SuperScript III First-Strand Synthesis Kit (Invitrogen, Carlsbad, CA). Following this, qPCR was executed using FastStart Universal SYBR Green kit (Roche, Indianapolis, IN). Primers were designed using the Primer Express 3.0 software (Thermo Fisher Scientific) and are listed in Table 1.

TABLE 1

List of qRT-PCR Primers

| Gene Name | Forward Primer | Reverse Primer |
|---|---|---|
| GAPDH | CCATCACCATCTTCCAGGAGCG SEQ ID NO: 2 | AGAGATGATGACCCTTTTGGC SEQ ID NO: 5 |
| IL8 | TCCTGATTTCTGCAGCTCTGT SEQ ID NO: 3 | AAATTTGGGGTGGAAAGGTT SEQ ID NO: 6 |
| TNFα | GACGCCCTCAATCAAAGTATAATTC SEQ ID NO: 4 | TCAAATTTCACTGCTTCATCCAGAT SEQ ID NO: 7 |

Docking Analysis

Chain A of PRMT5 protein in 4X61.pdb from the Protein Databank was used for docking. All docking experiments were performed using the Glide program (version 7.6) of the Schrodinger suite in standard precision mode (Small-Molecule Drug Discovery Suite 2017-3). The two compounds, Clo and Can, were docked into the PRMT5 active site under two conditions; 1. Docking the compound into PRMT5 active site in presence of SAM; and 2. Docking the compound into completely empty PRMT5 active site.

Statistical Analysis.

Prism 6 software (GraphPad, La Jolla, CA) was used to perform the statistical analysis. Statistics for the Kaplan-Meier survival curves were calculated using log-rank test. A two-tailed Student's t-test was used to compare two means and check for significant differences. All statistics were done using data from triplicate experiments and p value<0.05 was considered to be statistically significant. Results have been presented as mean±standard deviation (SD) or mean±standard error of mean (SEM), as specified.

Percent inhibition for compounds derived from the AlphaLISA HTS was calculated using the following formula: [({Avg. maximum reading−Inhibitor reading}/Avg. maximum reading)×100].

PRMT5 is a Negative Prognostic Factor in PDAC, CRC and BC Patients.

Figure 1B:
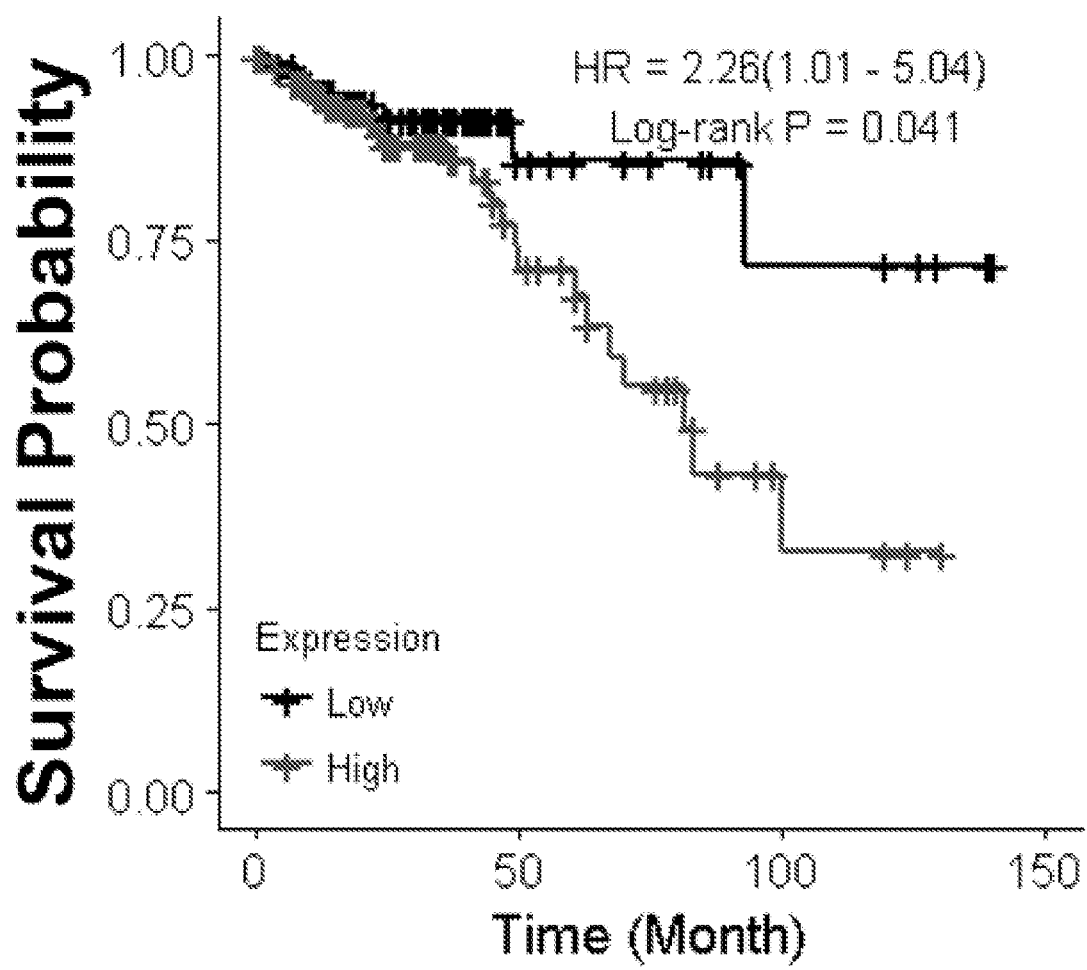
Figure 1C:
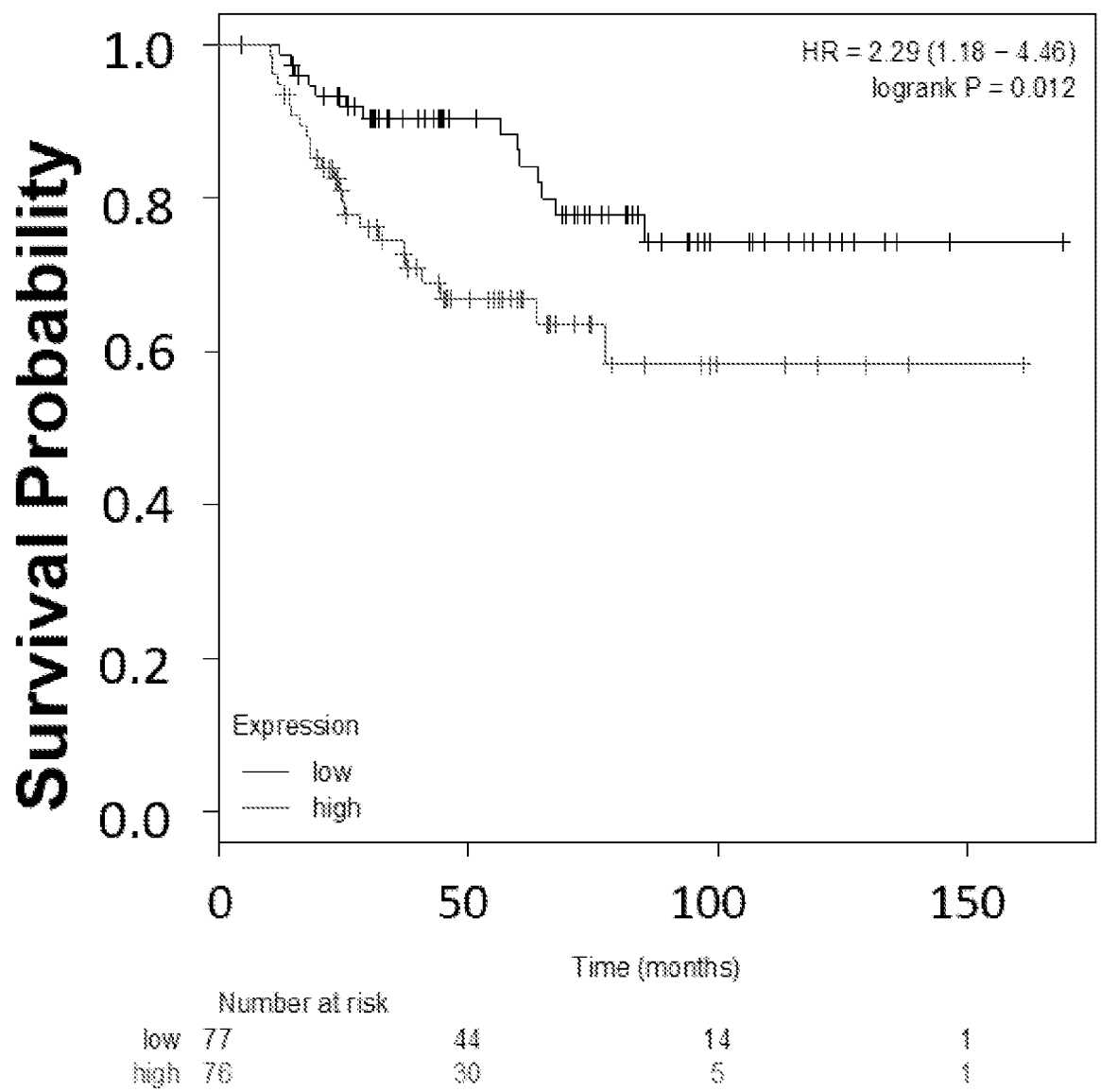

PRMT5 has been widely implicated as a tumor promoter in several cancers, including PDAC, CRC and BC. PRMT5 was recently shown to function as an inducer of the tumor phenotype, at least partly due to its increased expression and resulting methyltransferase activity, leading to activation of NF-κB pathway, and contributing to its constitutive signaling in PDAC, CRC and BC. As disclosed herein, a retrospective analysis was conducted to check for the correlation between PRMT5 protein expression and patient survival in these cancers. Using open access databases, Kaplan-Meier plots were constructed for each of these cancers and stratified the patient datasets based on low and high PRMT5 expression in the tumor tissue. As shown FIGS. 1A-1C, high PRMT5 expression was associated with poor survival in PDAC, CRC and triple negative breast cancer (TNBC) patients, as compared to patients in which PRMT5 was expressed at significantly lower levels. Interestingly, it was reported that using shRNA to knowdown PRMT5 could result in significant inhibition of tumor cell growth in the estrogen receptor positive (ER+) breast cancer MCF7 cells. These observations, in combination with previously documented role of PRMT5 as a critical tumor promoter, reiterate the therapeutic significance of inhibiting PRMT5 expression in cancer, such as PDAC, CRC, TNBC, and ER+BC, etc. The probe for FDA-approved drugs that could selectively inhibit PRMT5 is described in the following sections, thereby having the capacity to move faster through the clinical trial process with potential candidate compounds.
Identification of Top Two FDA-Approved Hits with PRMT5-Inhibitory Activity In Vitro Using AlphaLISA HTS.

To design a drug screen to check for compounds that had the potential to inhibit PRMT5 methyltransferase activity, the AlphaLISA assay was utilized. Optimization of the AlphaLISA protocol to be used has been previously published. The principle of this assay is illustrated in FIG. 2 and utilizes a well-known PRMT5 substrate H4R3 that is biotinylated, the methyl group donor SAM, PRMT5 and Acceptor/Donor beads. Addition of PRMT5 and SAM enables symmetric dimethylation of biotin-H4R3 to form biotin-H4R3-me2. Acceptor beads with a specific antibody tag for dimethylated H4R3 recognize the symmetric dimethylated mark and bind to it. Donor beads have a streptavidin tag that allows for binding to biotinylated H4R3. Excitation with 680 nm emits a singlet oxygen from the Donor beads that is accepted by the Acceptor beads bound to the same peptide on the dimethyl mark, in turn causing an emission of light at 615 nm. This emitted AlphaLISA signal is directly proportional to the methyltransferase activity of PRMT5, thus allowing for quantification of its enzymatic activity.

Using this PRMT5-specific AlphaLISA assay, chemical libraries containing FDA-approved compounds were screened. Upon calculating percent inhibition from initial screening studies, Clo and Can were identified as the two top PRMT inhibitors (Table 2).

TABLE 2

Known Indications of Top Two FDA-Approved Candidates from AlphaLISA ™ HTS

| Drug name | Indication |
| --- | --- |
| Cloperastine hydrochloride | Cough Suppressant |
| Candesartan cilexetil | Hypertension |

Abbreviations: AlphaLISA, amplified luminescent proximity homogeneous assay-linked immunosorbent assay; FDA, Food and Drug Administration; HTS, high throughput screening.

Their ability to reduce the AlphaLISA signal was further validated by using concentration-dependent curves for these drugs. As expected, a decrease in AlphaLISA signal with increasing concentrations of Clo (FIG. 3A) and Can (FIG. 3B) respectively was observed. The respective $IC_{50}$s are summarized in FIG. 3C.

Clo is used for the treatment of cough. On the other hand, Can is an angiotensin II receptor blocker used in the treatment of hypertension. These hits were exciting to explore for alternative indications as these drugs are already approved by the FDA. This in turn would truncate the timeline for clinical trials if found to have promising therapeutic implications. The selectivity of these drugs to inhibit PRMT5 and in turn NF-κB was checked, thereby having a negative effect on the cancer phenotype and subsequent therapeutic potential.

Viability of Cancer Cell Lines with Clo and Can Treatment.

Figure 4B:
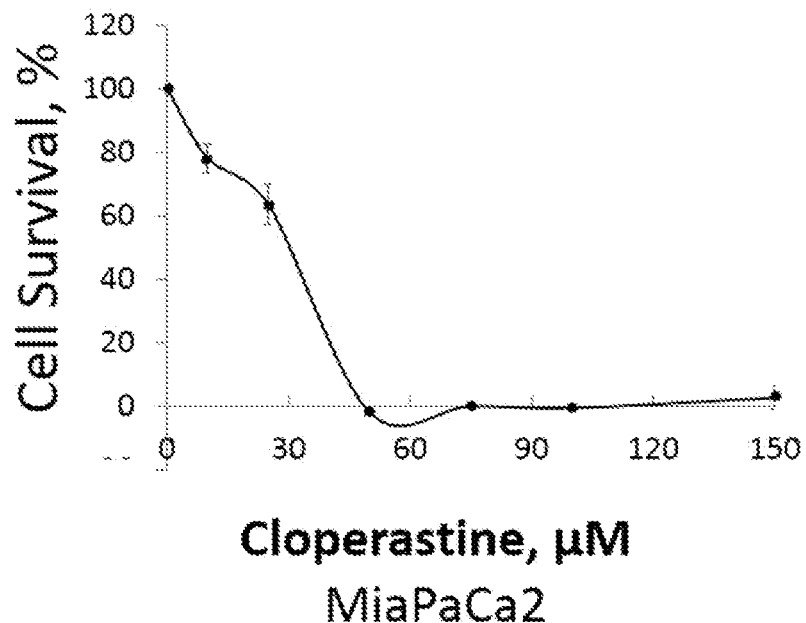
(FIG. 4B), and AsPC1 (FIG. 4C), on CRC cells including HT29 (FIG. 4D), HCT116 (FIG. 4E), and DLD1 (FIG. 4F) and BC cells including (MDA-MB-231 (FIG. 4G), and BT20 (FIG. 4H). Similarly, data is presented for the effect of Can on PDAC cells including PANC1 (FIG. 4I), MiaPaCa2.
Figure 4C:
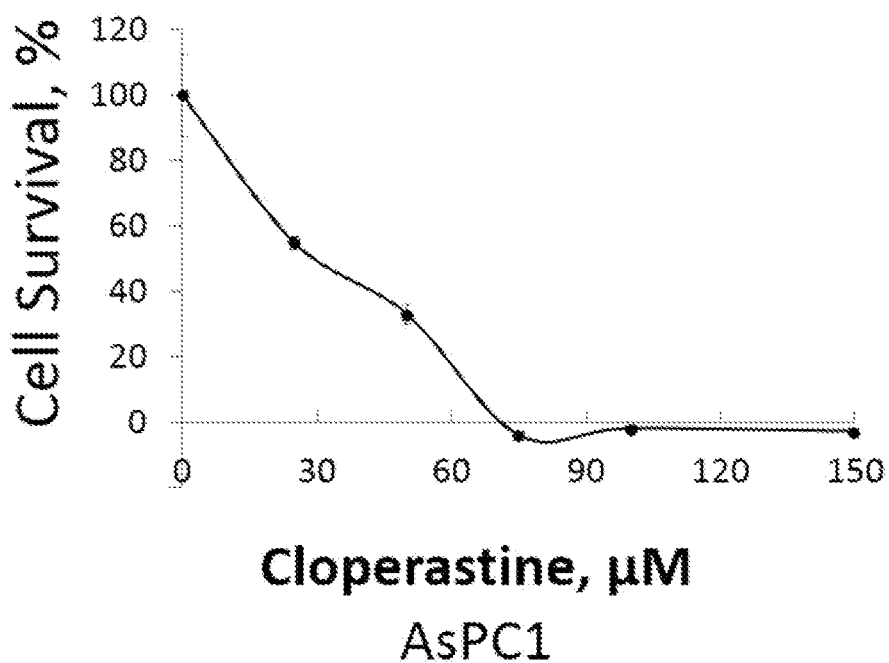
(FIG. 4J), and AsPC1 (FIG. 4K), on CRC cells including HT29 (FIG. 4L), HCT116 (FIG. 4M), and DLD1 (FIG. 4N) and BC cells including MDA-MB-231 (FIG. 4O), and BT20 (FIG. 4P). PDAC cells (PANC1, MiaPaCa2 and AsPC1) exhibited an $IC_{50}$~30 µM and ~20 µM respectively for both these drugs (FIGS. 4A-4C and FIGS. 4I-4K). CRC cell lines (HT29, HCT116 and DLD1) showed $IC_{50}$ be 18-34 µM for Clo and 15-17 µM for Can (FIGS. 4D-4F and 4L-4N). Similarly, BC cells (MD-MB-231 and BT20) ranged between 26-29 µM and 18-20 µM for Clo and Can respectively (FIGS. 4G-4H and 4O-4P).
Figure 4D:
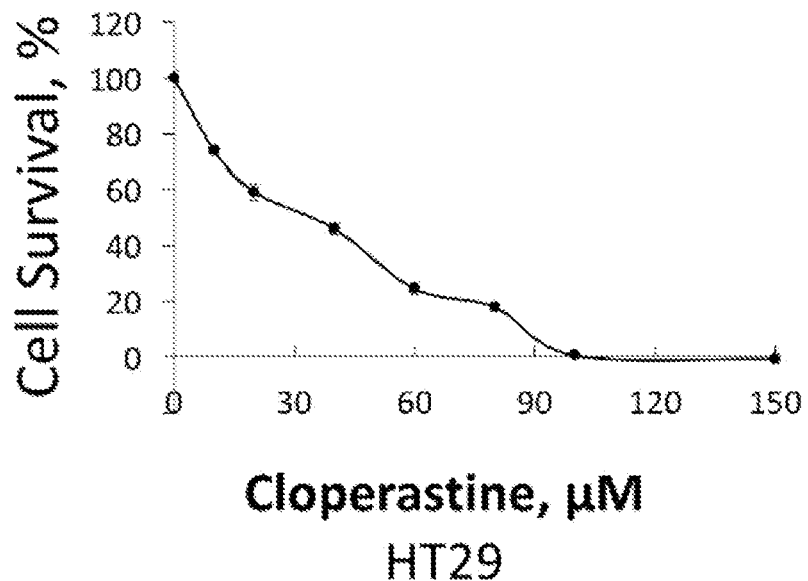
Figure 4E:
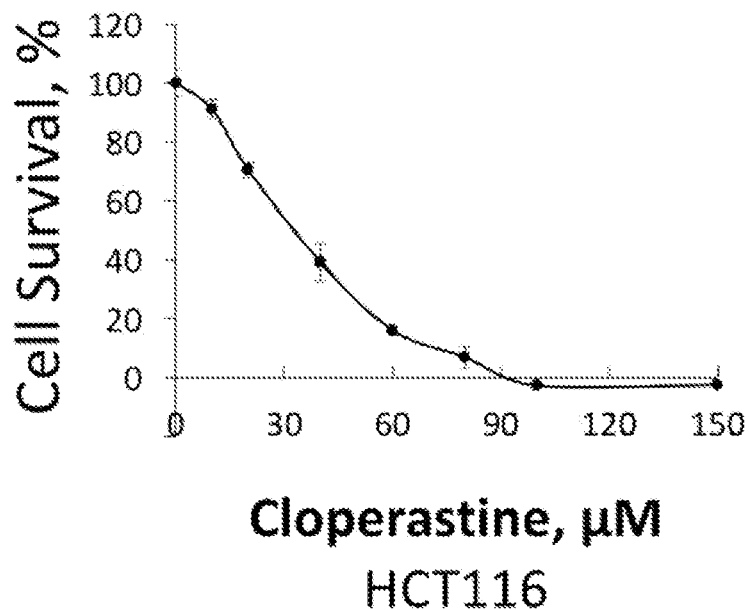
Figure 4F:
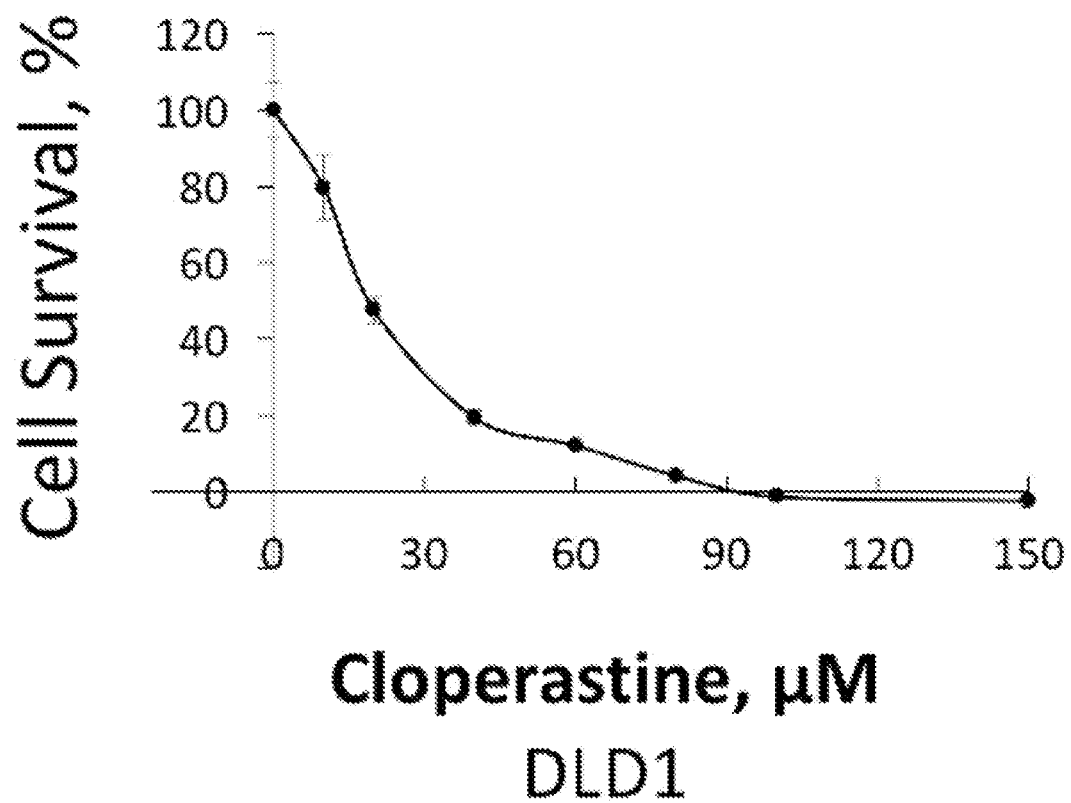
Figure 4G:
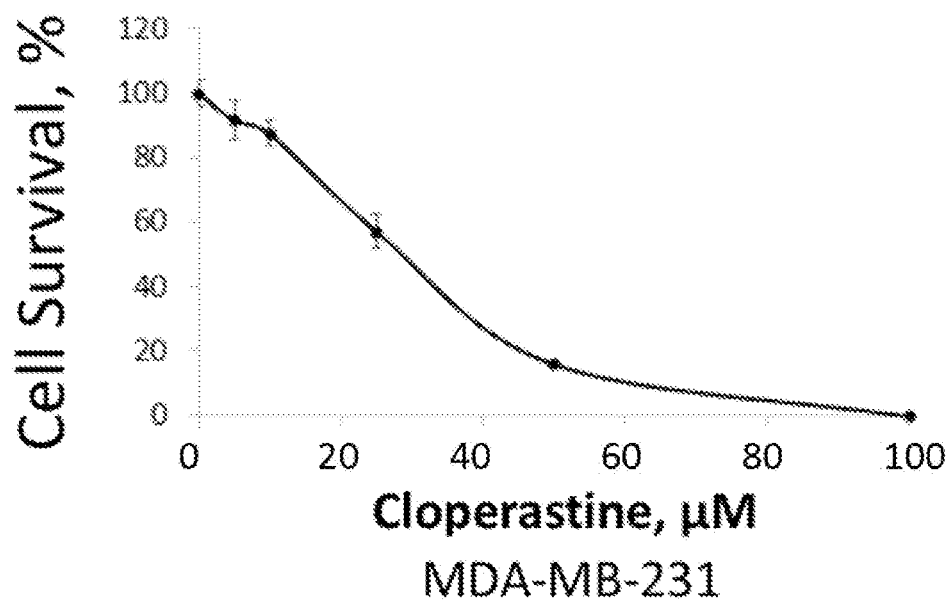
Figure 4H:
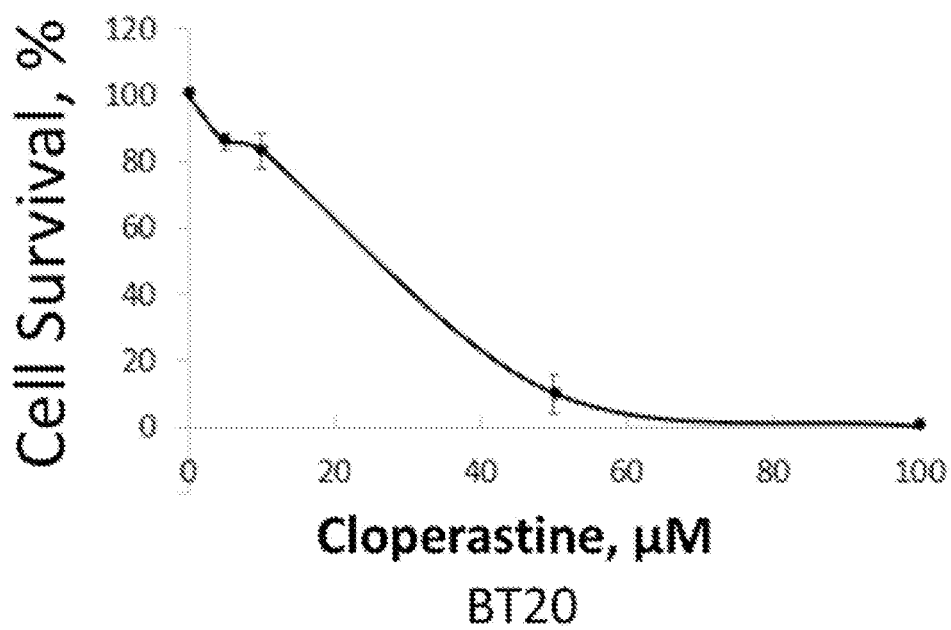
Figure 4I:
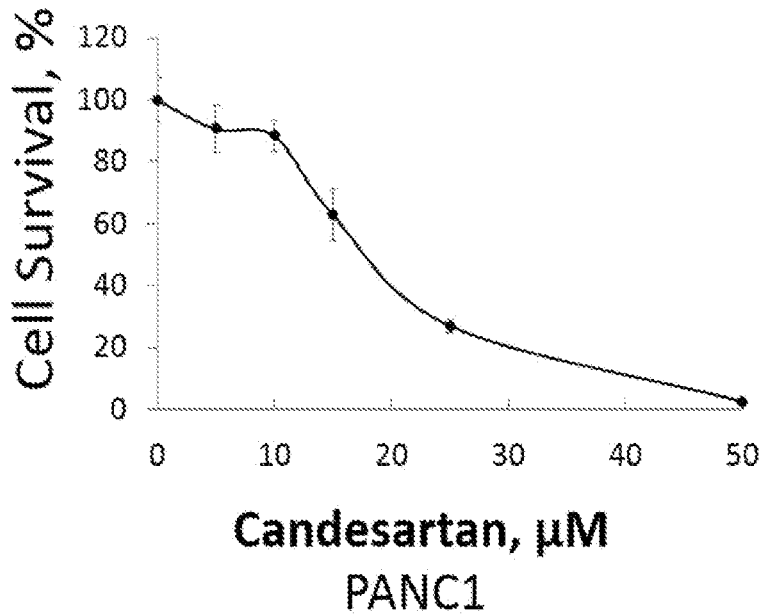
Figure 4J:
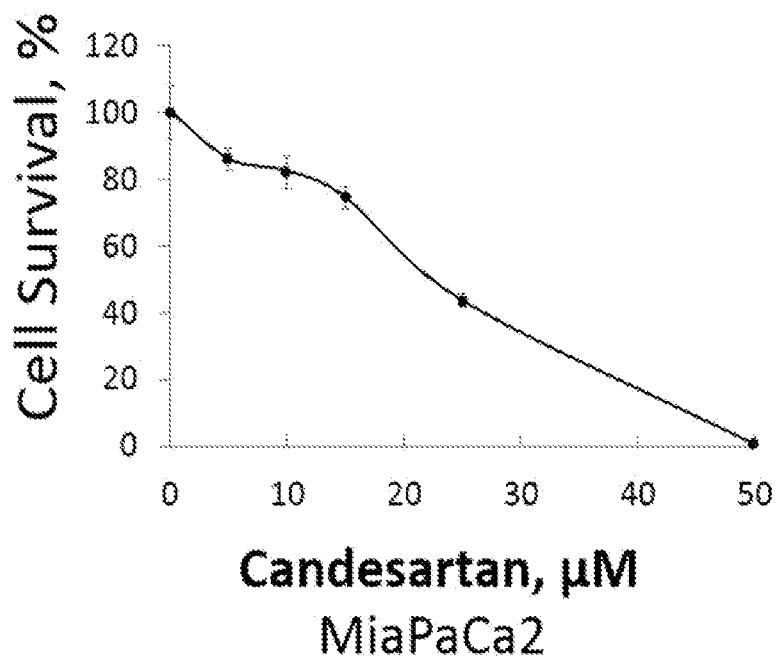
Figure 4K:
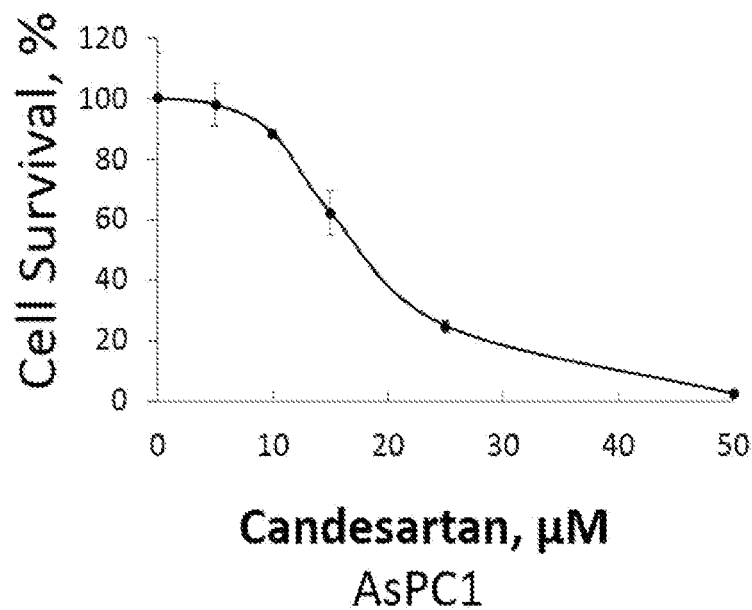
Figure 4L:
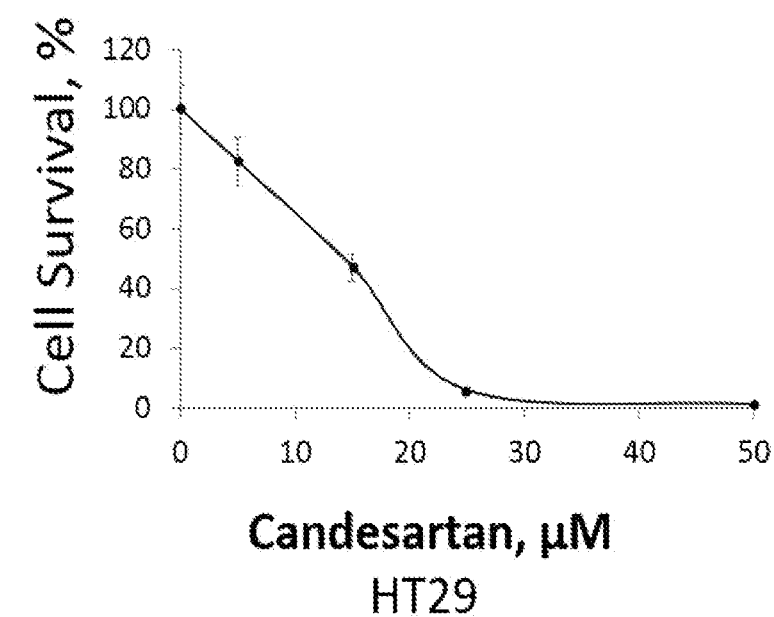
Figure 4M:
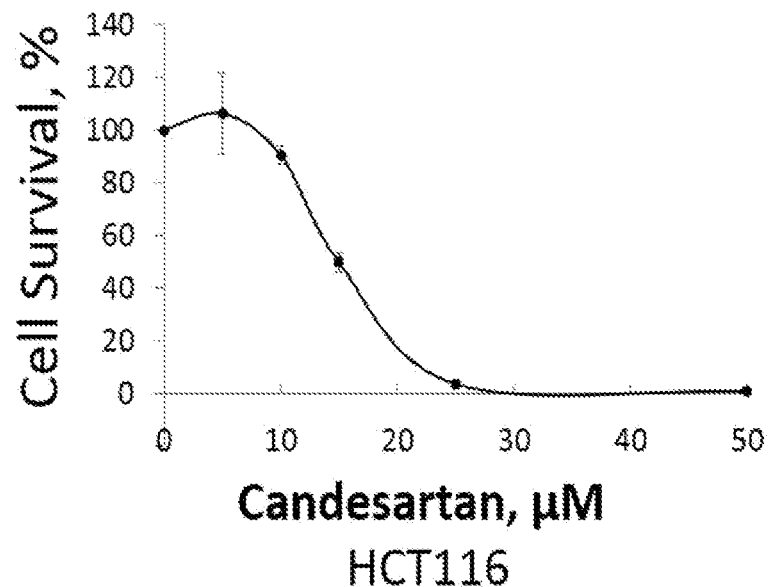
Figure 4N:
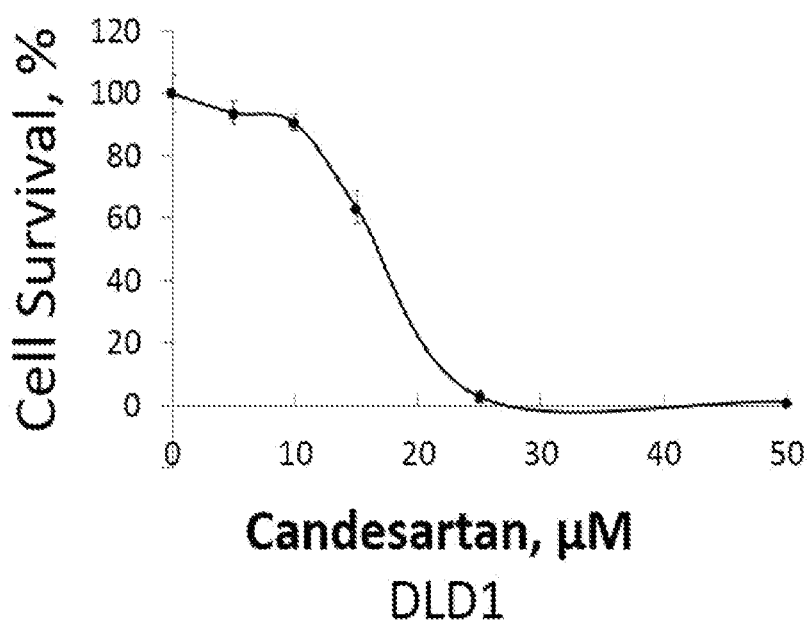
Figure 4O:
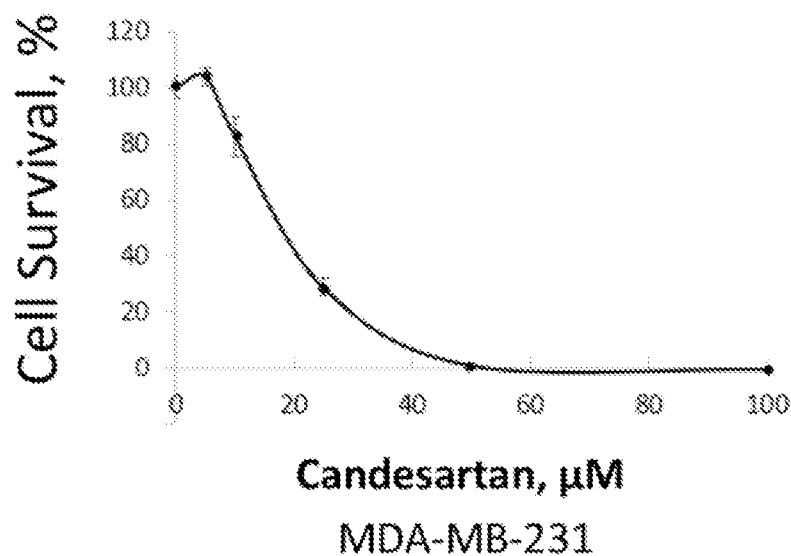
Figure 4P:
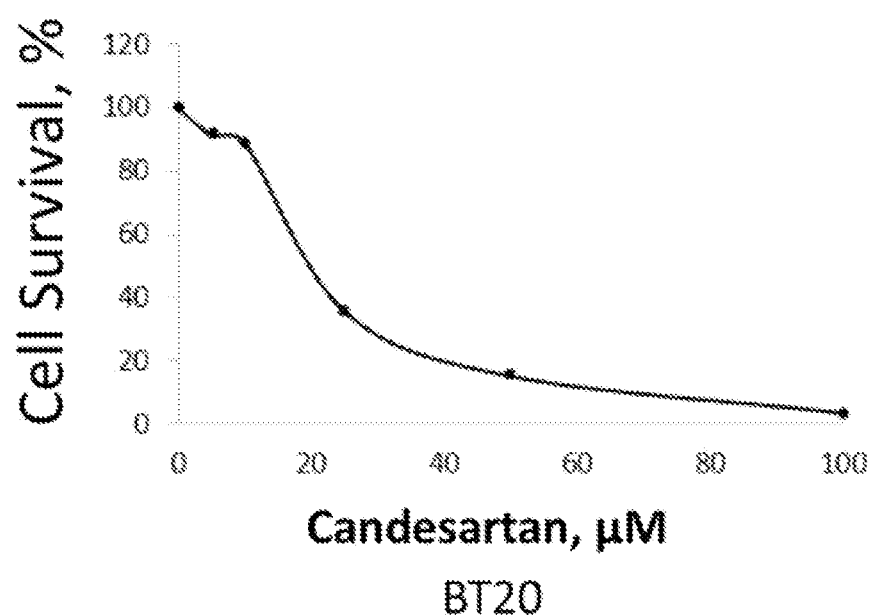
Figures 4Q, 5A:
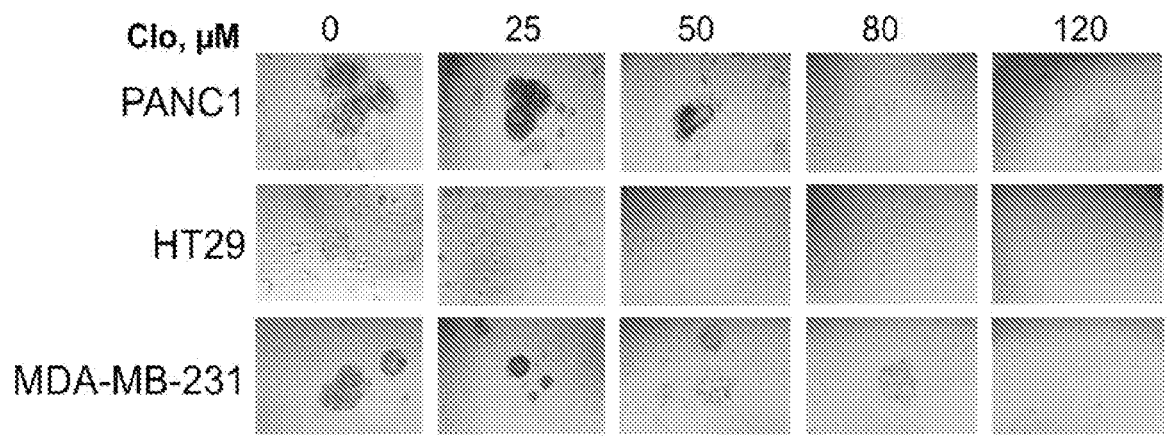
FIGS. 5A-5H show a 3D colony assay signifying a substantial decrease in colony formation ability, in images of colonies for PANC1, HT29, and MDA-MB-231 (FIG. 5A), and in quantified curves for PANC1 (FIG. 5B), HT29 (FIG. 5C) as well as MDA-MB-231 cells (FIG. 5D) with increasing concentrations of Clo and a substantial decrease in colony formation ability in images of colonies for PANC1, HT29, and MDA-MB-231 (FIG. 5E), in quantified curves for PANC1 (FIG. 5F), HT29 (FIG. 5G) as well as MDA-MB-231 cells (FIG. 5H) with increasing concentrations of Can.
Figure 5B:
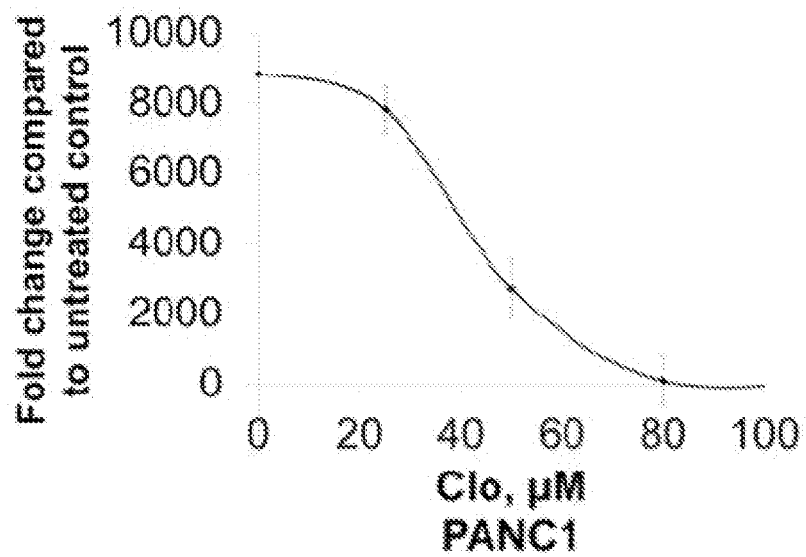
Figure 5C:
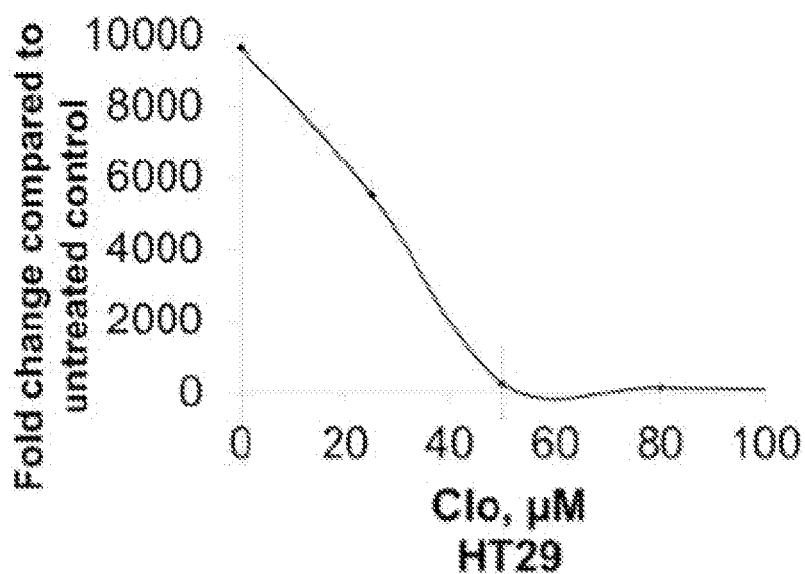
Figure 5D:
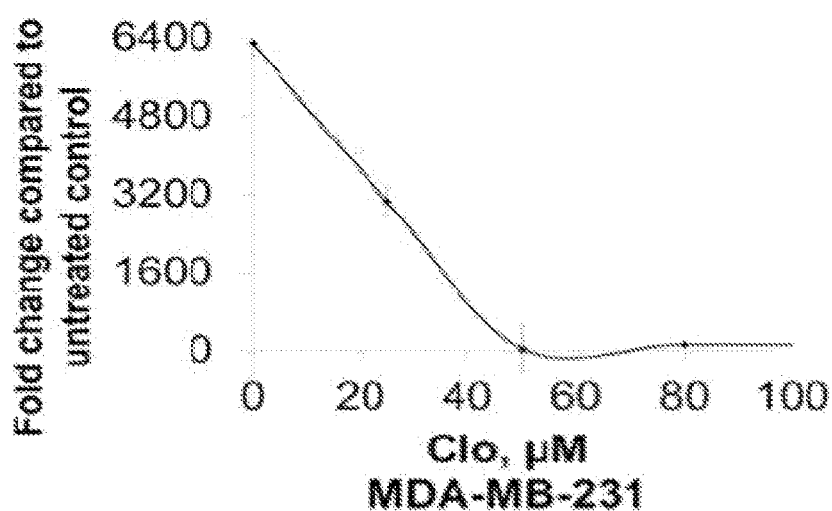
Figure 5E:
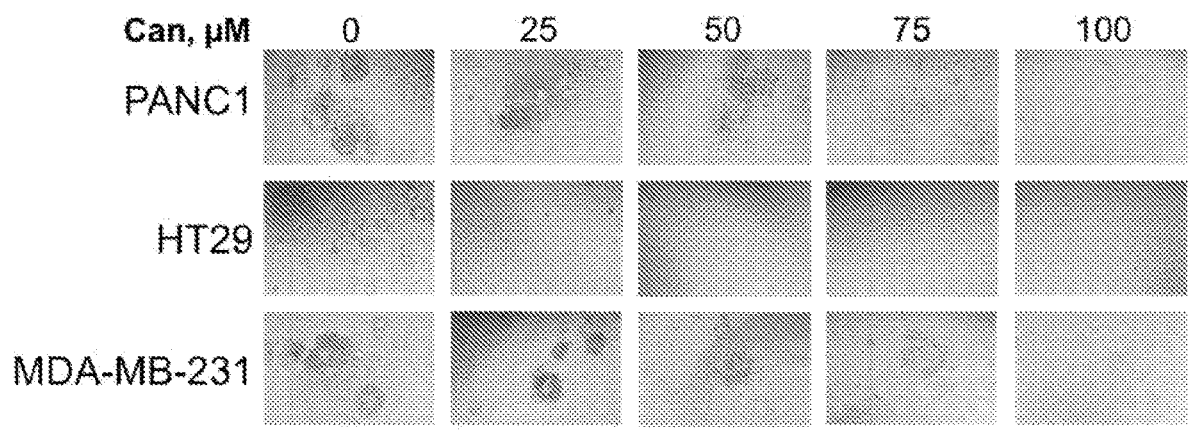
Figure 5F:
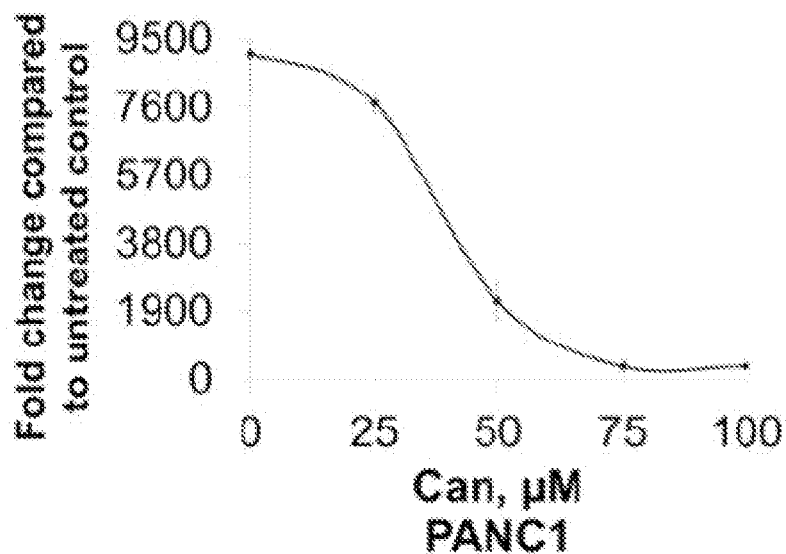
Figure 5G:
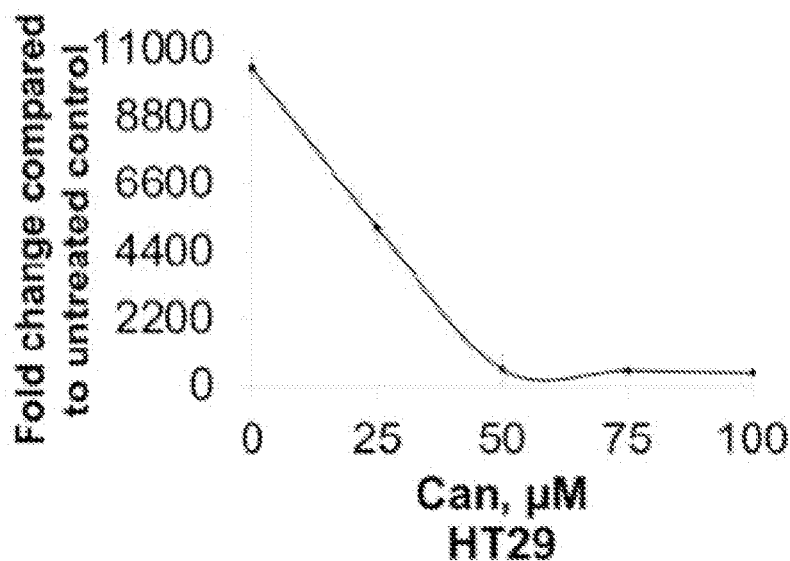
Figure 5H:
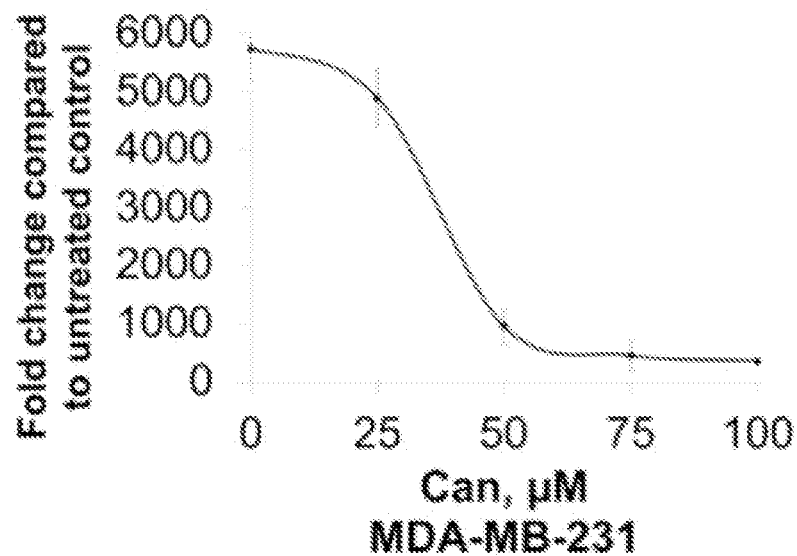

Since AlphaLISA protocol is a non-cell, plate-based assay, the effect of Clo and Can in cell-based assays was checked. The effect of these drugs on cell viability of well-known PDAC, CRC and BC cell lines using the MTT assay was first determined. It was observed that with increasing concentrations of Clo as well as Can, there was a concurrent decrease in cell viability of PDAC cells. Data is presented for the effect of Clo on PDAC cells including PANC1 (FIG. 4A), MiaPaCa2; (FIG. 4B), and AsPC1 (FIG. 4C), on CRC cells including HT29 (FIG. 4D), HCT116 (FIG. 4E), and DLD1 (FIG. 4F) and BC cells including (MDA-MB-231 (FIG. 4G), and BT20 (FIG. 4H). Similarly, data is presented for the effect of Can on PDAC cells including PANC1 (FIG. 4I), MiaPaCa2; (FIG. 4J), and AsPC1 (FIG. 4K), on CRC cells including HT29 (FIG. 4L), HCT116 (FIG. 4M), and DLD1 (FIG. 4N) and BC cells including (MDA-MB-231 (FIG. 4O), and BT20 (FIG. 4P). PDAC cells (PANC1, MiaPaCa2 and AsPC1) exhibited an $IC_{50}$~30 µM and ~20 µM respectively for both these drugs (FIGS. 4A-4C and FIGS. 4I-4K). CRC cell lines (HT29, HCT116 and DLD1) showed $IC_{50}$ be 18-34 µM for Clo and 15-17 µM for Can (FIGS. 4D-4F and 4L-4N). Similarly, BC cells (MD-MB-231 and BT20) ranged between 26-29 µM and 18-20 µM for Clo and Can respectively (FIGS. 4G-4H and 4O-4P). FIG. 4Q is a summary table listing $IC_{50}$ values from FIGS. 4A-4P.

Overall, this study highlighted efficacy of both these drugs to inhibit cell viability of PRMT5-overexpressing PDAC, CRC and BC cell lines.

3D Culture Growth of Cancer Cell Lines with Clo and Can Treatment.

Recent validation studies with 3D spheroidal cultures demonstrate their ability to closely mimic critical characteristics of the in vivo tumor microenvironment, including a hypoxic core and decreased cell-cell contact. These properties contribute to the proliferation and metastatic potential of cancer cells. Hence, it was tested to determine whether treatment with either Clo and/or Can had a restrictive effect on the 3D colony potential in PDAC, CRC and BC cells. It was observed that increasing concentrations of both Clo (FIGS. 5A-5D) and Can (FIGS. 5E-5H) caused a marked decrease in the extent of 3D colony formation in representative PDAC, CRC and BC cell lines, PANC1, HT29 and MDA-MB231 respectively, highlighting the promising efficacy of both these drugs to limit the 3D culturing potential of these cells.

Effect of Clo and Can Treatment on Symmetric Dimethylation of PRMT5 In Vitro.

Figure 6:
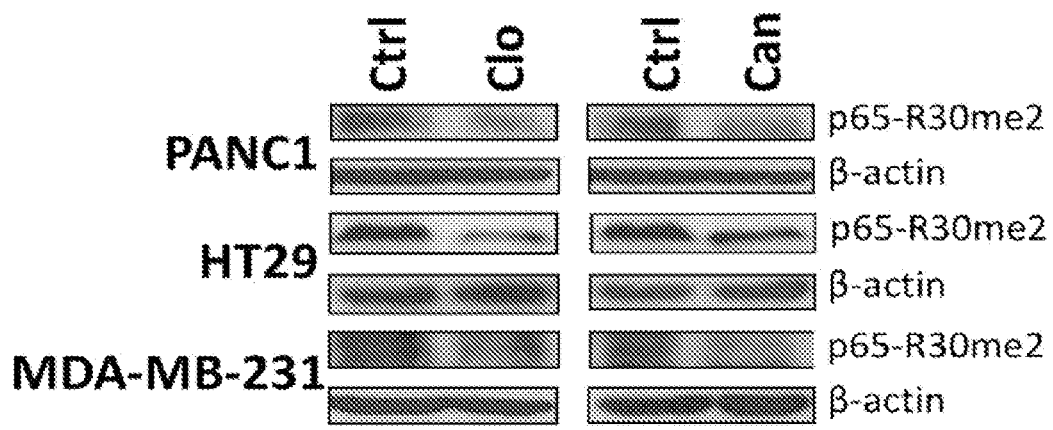
FIG. 6 shows a Western blot showing that treatment with MTT $IC_{50}$ values of Clo and Can decreased symmetric dimethylation of p65, a PRMT5 substrate, in PANC1, HT29 as well as MDA-MB-231 cells.
Figure 7A:
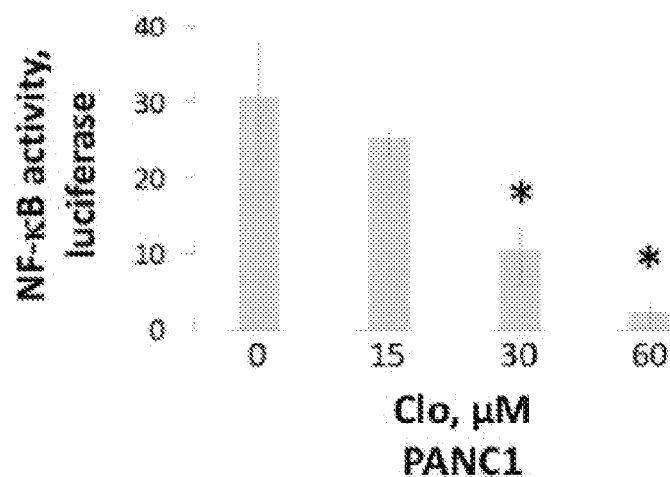
FIGS. 7A-7F show the results of a luciferase assay depicting reduction in NF-κB activation with increasing concentrations of Clo PANC1, HT29 and MDA-MB-231 cells (shown in FIGS. 7A-7C, respectively) and increasing concentrations of Can (shown in FIGS. 7D-7F, respectively). Data represent means±S.D. for three independent experiments. *P<0.05 vs. Control "0 µM" group.
Figure 7B:
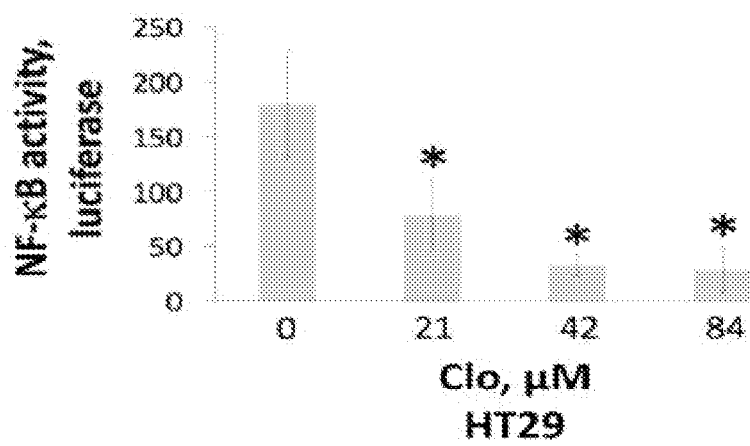
Figure 7C:
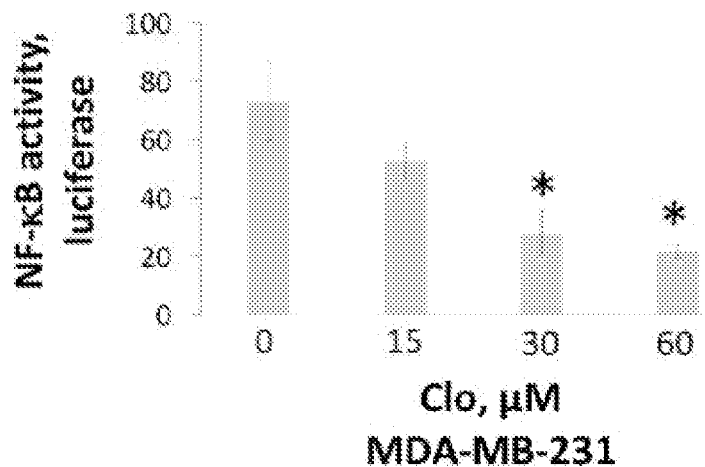
Figure 7D:
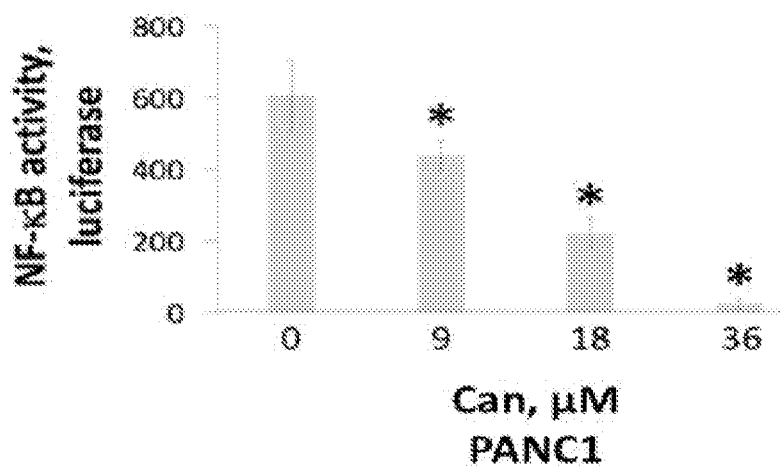
Figure 7E:
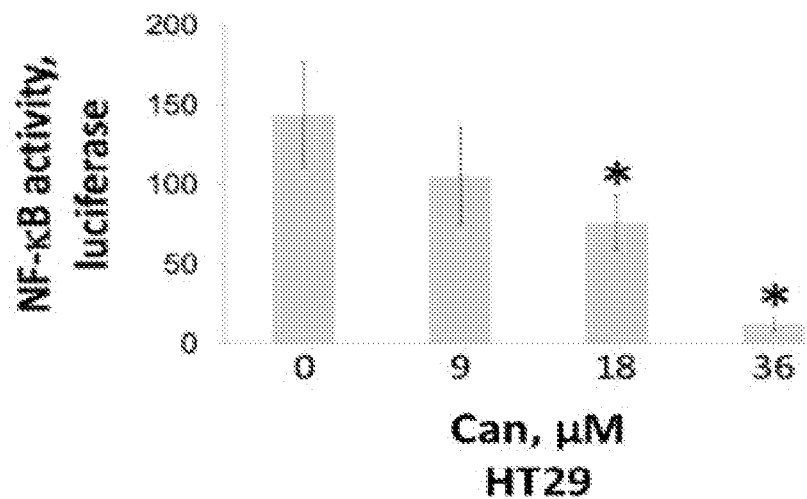
Figure 7F:
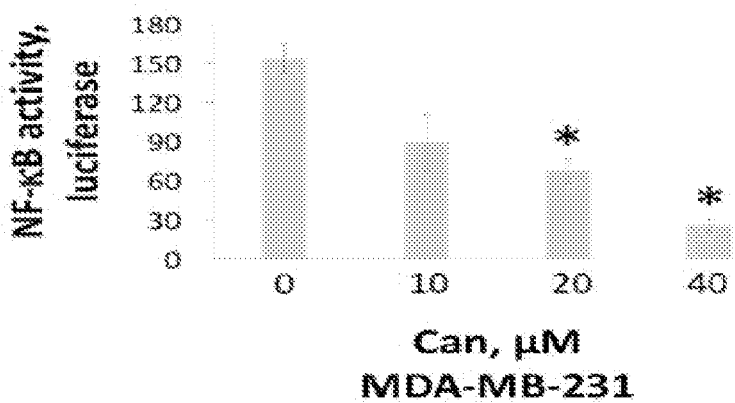
Figure 8A:
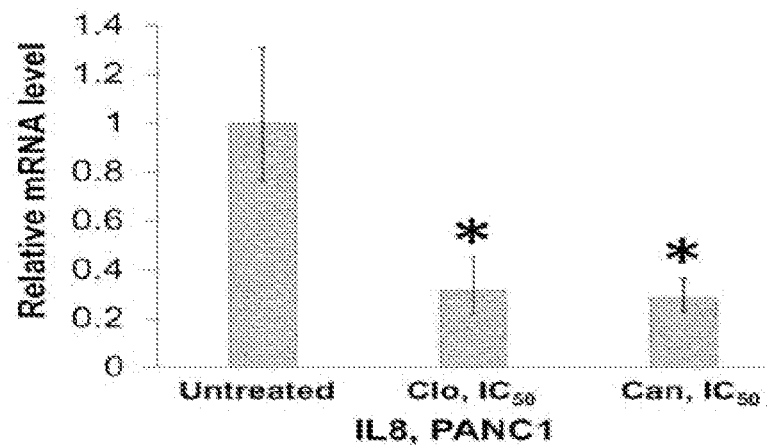
FIGS. 8A-8F illustrate qPCR assays showing reduction in activation of NF-κB dependent genes, IL8 and TNFα in PANC1 (shown in FIGS. 8A & 8B, respectively), IL8 and TNFα in HT29 (shown in FIGS. 8C & 8D, respectively), IL8 and TNFα in MDA-MB-231 cells (shown in FIGS. 8E & 8F), upon treatment with Clo and Can. Data represent means±S.D. for three independent experiments. *P<0.05 vs. Control "0 µM" group.
Figure 8B:
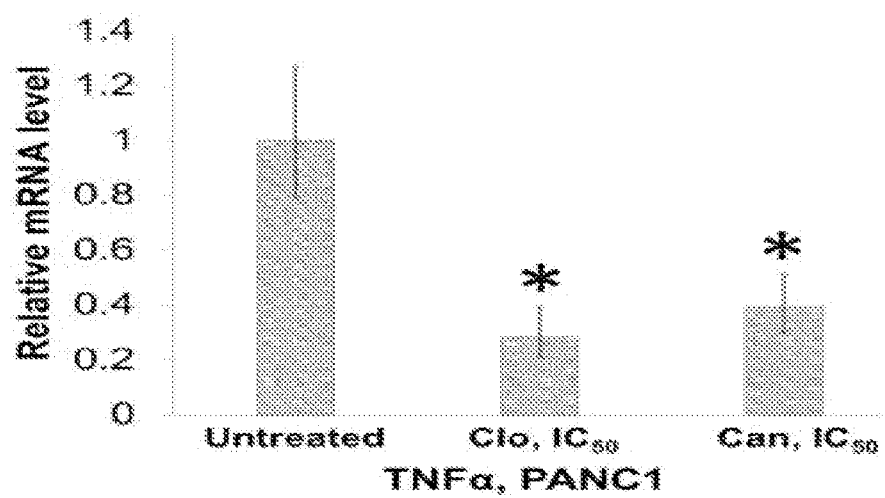
Figure 8C:
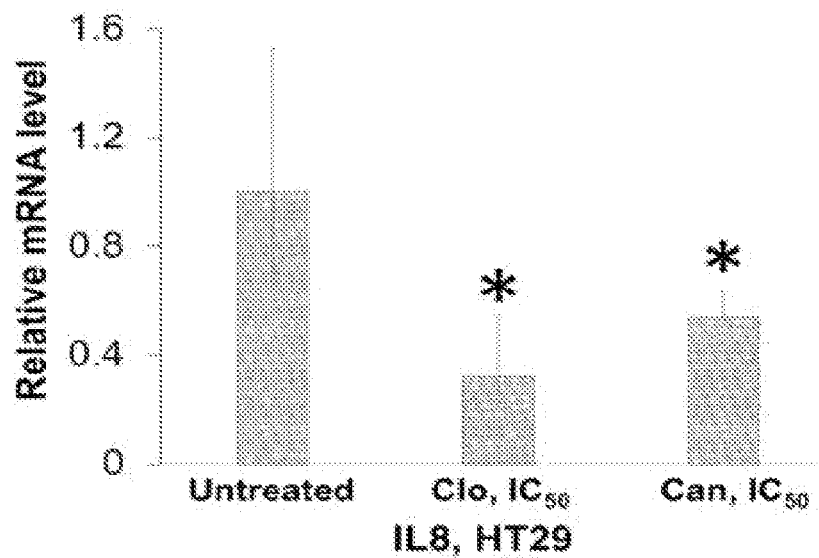
Figure 8D:
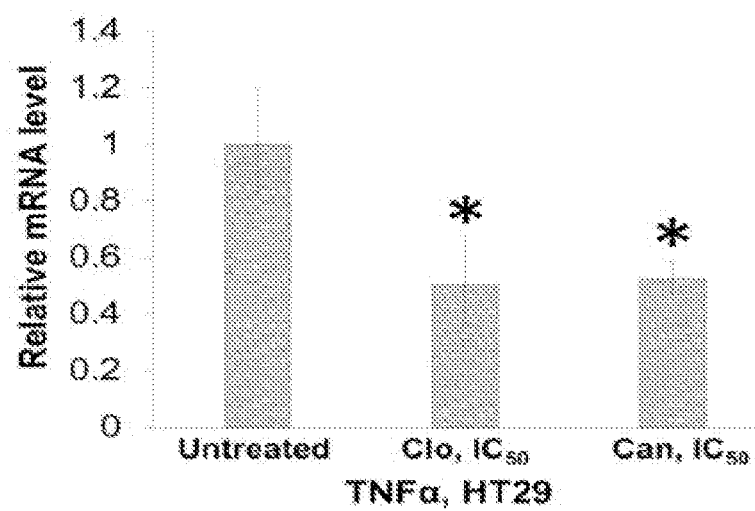
Figure 8E:
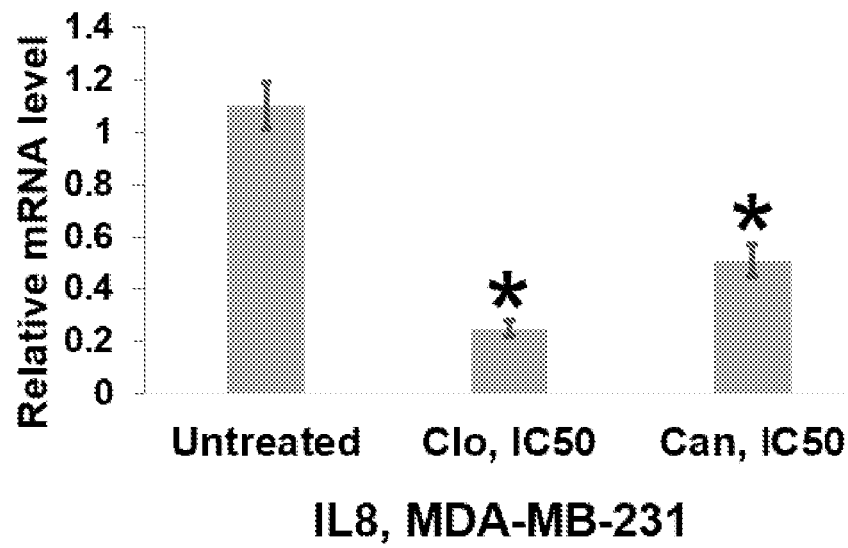
Figure 8F:
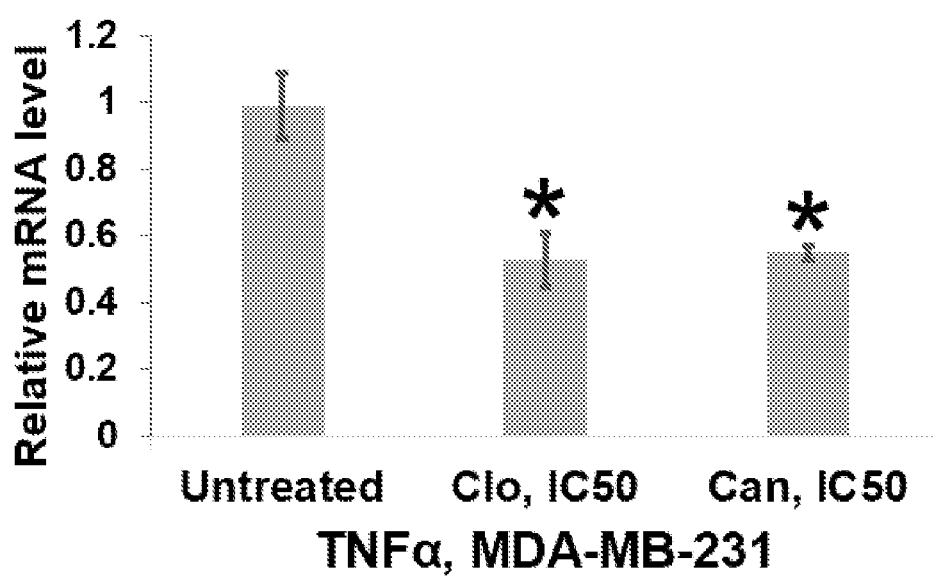

Previously we have shown that PRMT5 activates NF-κB through methylation of its p65 subunit at R30. Therefore, we expect that treatment with PRMT5 inhibitors such as Clo and Can would negatively affect PRMT5-mediated methylation of NF-κB in cancer cells. A specific antibody was generated to detect the R30 dimethyl tag introduced by PRMT5 in collaboration with GenScript Inc. Using this antibody, Western blotting studies were conducted to detect effect of Clo and Can on R30 dimethylation in cancer cells. With selective PRMT5 inhibition, treatment with both drugs led to decrease in its methyltransferase activity respectively, as indicated with reduction in the dimethylation levels at R30 in PANC1, HT29 and MDA-MB-231 cells, as compared to untreated condition (FIG. 6). Overall, these results indicate that both Clo and Can were selective PRMT5 methyltransferase activity inhibitors. Effect of Clo and Can Treatment on NF-κB Activation. Increased PRMT5-mediated methylation of NF-κB has been associated with its increased activation. To check if decrease in methylation of the p65 subunit by Clo and Can (FIG. 6) had a corresponding effect on NF-κB activation, the κB luciferase assay was used. It was noted that there was a concurrent decrease in the activation of NF-κB, with increasing concentrations of both Clo (FIGS. 7A-7C) and Can (FIGS. 7D-7F) in PANC1, HT29 and MDA-MB-231 cells.

Furthermore, NF-κB activation is a critical step in its function as a transcription factor that leads to activation of genes implicated in promoting all hallmarks of cancer. It was checked whether decrease in NF-κB activation due to potential PRMT5 inhibition by Clo and Can (FIGS. 7A-7F) affected its function as a transcription factor and correlated with decreased downstream target gene expression. To check this proposed effect, PANC1, HT29 and MDA-MB-231 cells were treated with Clo and Can respectively, followed by qPCR to check for expression of well-known NF-κB target genes implicated in cancers, IL8 and TNFα. As expected, there was a significant decrease in mRNA expression of both IL8 and TNFα in both the drug-treated cancer cell lines, as compared to untreated condition (FIGS. 8A-8F).

Overall, the evidence supports that the selective inhibition of PRMT5 methyltransferase activity by Clo and Can, via decrease in methylation of a key substrate, NF-κB and its subsequent activation and downstream target gene expression, negatively impact the PDAC, CRC and BC phenotypes respectively.

Predicted Binding of Clo and can to PRMT5.

Computer-based docking studies were used to identify residues on PRMT5 structure that are critical in binding interactions of Clo and Can with PRMT5. The best energetically favorable interactions for Clo in presence and absence of the methyl donor SAM were analyzed. It is interesting to note here that Clo partially overlaps with SAM binding site in absence of SAM. This could be a possible mechanism by which Clo could interfere with SAM binding to PRMT5, thereby inhibiting its methyltransferase activity. If binding scores for both these conditions are considered, they are very close to each other and thus it is hard to predict which condition is more favorable. Similarly, for Can, it was observed that the binding pose did not show much overlap in the area where SAM was bound to PRMT5. However, in the absence of SAM, Can showed some overlap, and could interfere through a similar mechanism as Clo proposed earlier. Binding affinity for Apo form was higher than the SAM-bound condition, suggesting that the former might be a more energetically favorable and thus likely occurrence compared to the latter.

Ligand affinity maps were plotted to better understand which PRMT5 residues potentially interact with the Clo and Can respectively, in presence and absence of SAM. Notably, two PRMT5 residues that stood out from these docking studies were glutamine (E) 444 and phenylalanine (F) 327. The E444 residue belongs to the catalytic cleft of PRMT5 and plays a key role in the methyltransferase activity of the enzyme. On the other hand, the F327 residue plays a crucial role for PRMT5 product specificity. Overall, these ligand affinity maps hint towards residues that play a prime role in the enzyme-drug interactions and serve as a basis for designing future studies to validate these findings in vitro.

EXAMPLE 3

Inhibition of Xenograft Tumor Growth in PDAC, CRC, BC with Protein Arginine Methyl Transferase Inhibitors In Vivo Male and female NSG mice were obtained from the In Vivo Therapeutics Core at Indiana University School of Medicine. After acclimation for 7 days, NSG mice (5-6 weeks old) were xenografted with *Mycoplasma*-free PANC1, MCF7 or HT29 cells subcutaneously ($1\times10^7$ PANC1, $3\times10^6$ MCF7 or $3\times10^6$ HT29 cells used per mouse in 0.2 ml of a 1:1 mix of serum free DMEM media, or serum free RPMI media and Matrigel). Male mice were xenografted with PANC1 and HT29 cells. Female mice were xenografted with MCF7 cells. 5 mice were randomized in each group when tumor volumes reached ~50 mm³. Mice were treated with either vehicle control (10% DMSO, 20% PEG400, 5% Tween 80 and 65% sterile water), 100 mg/kg or 200 mg/kg candesartan cilexetil dissolved in the vehicle, or 100 mg/kg or 200 mg/kg cloperastine dissolved in the vehicle through oral gavage daily. Tumor volumes were measured 4 times per week and body weights were measured twice a week. The study was performed in accordance with the guidelines and standards of the Institutional Animal Care and Use Committee (IACUC)

Figure 9A:
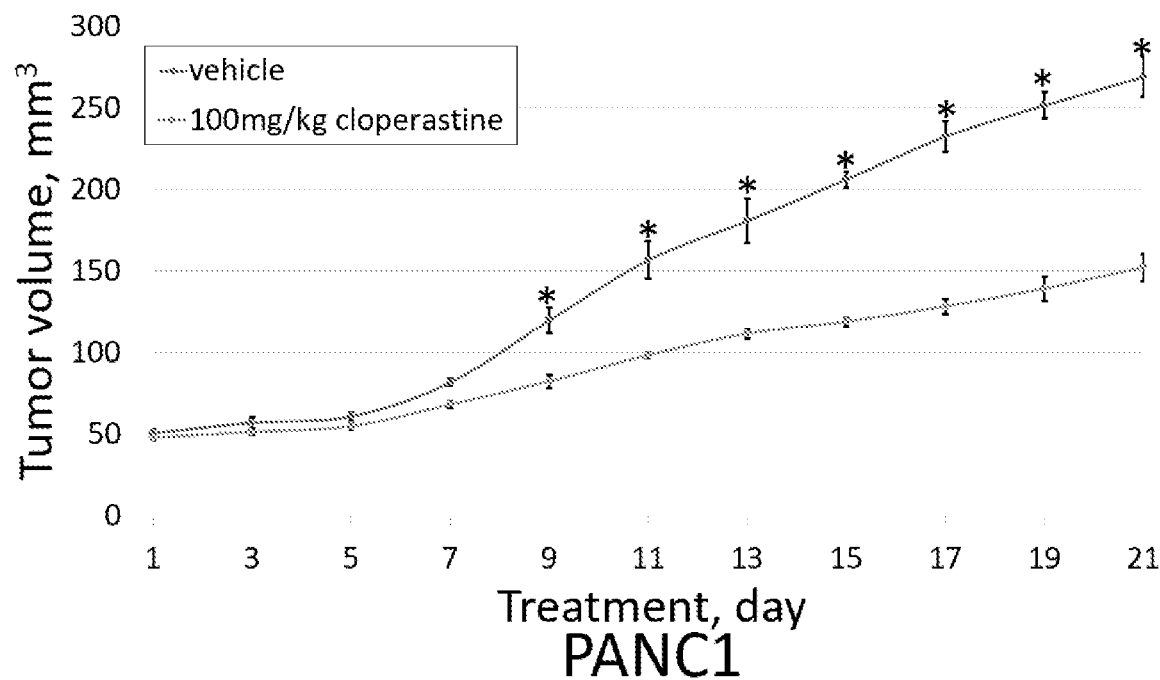
FIGS. 9A-9F provide data demonstrating how Clo inhibits tumor growth in different in vivo mice cancer models.
Figure 9B:
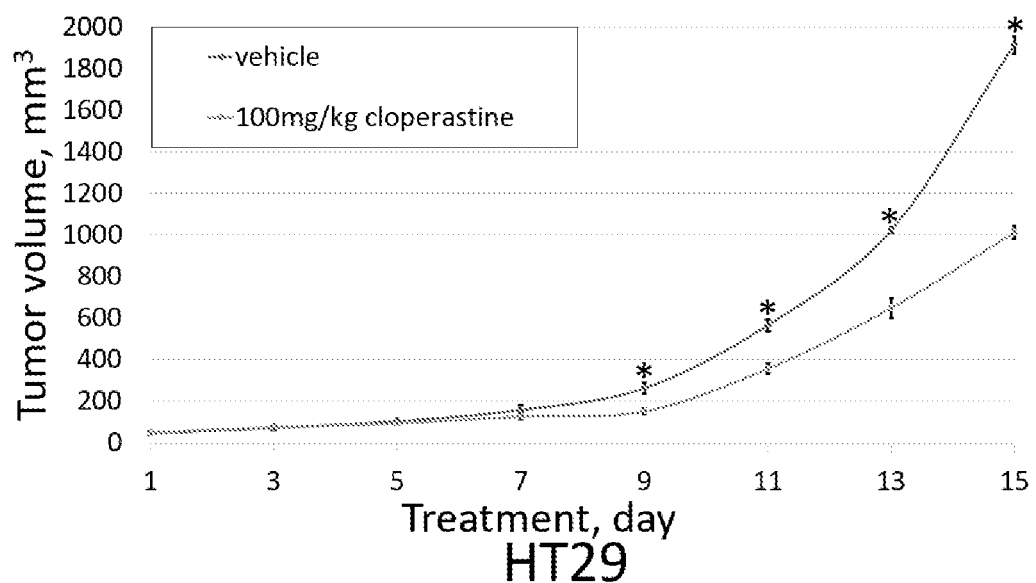
Figure 9C:
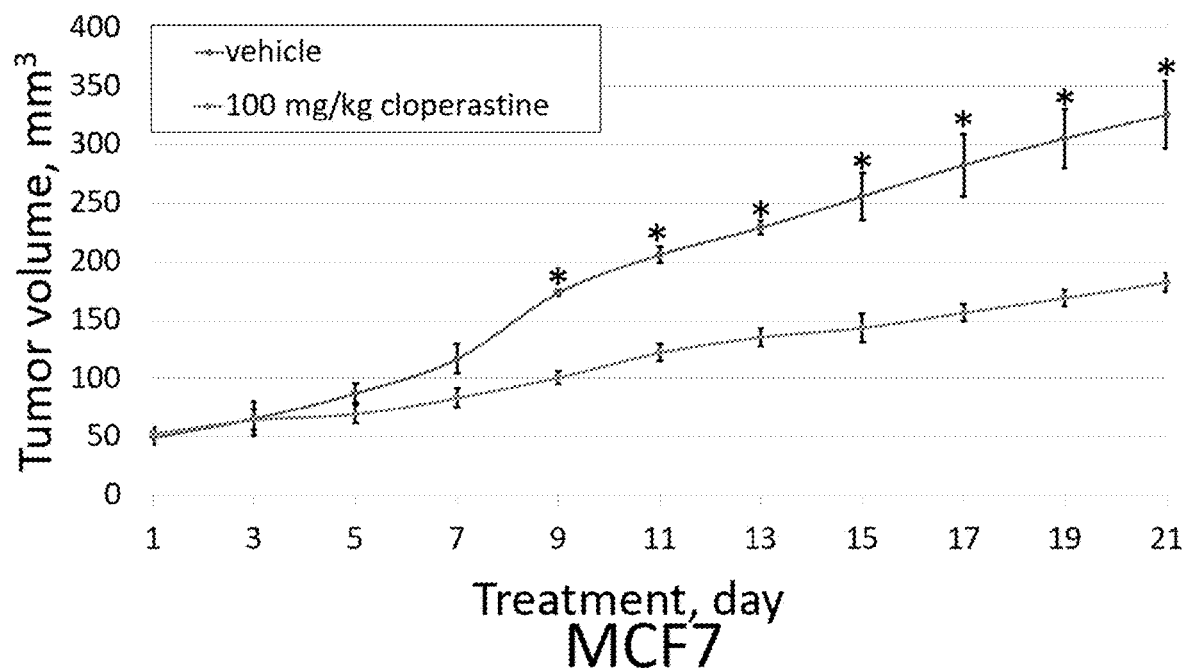
Figure 9D:
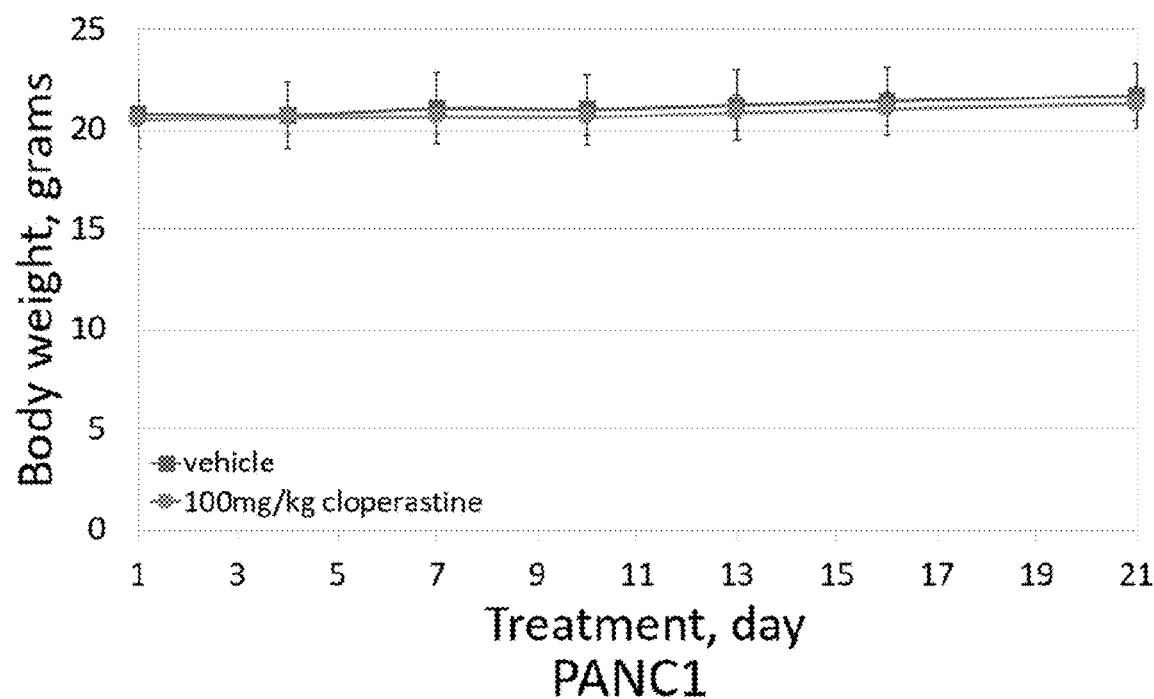
Figure 9E:
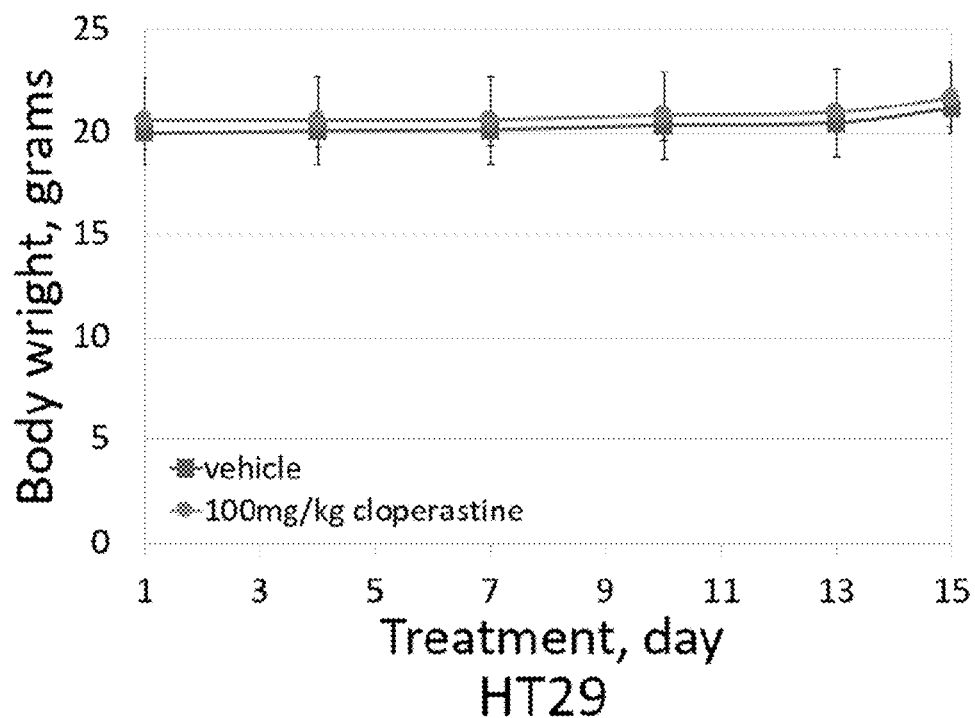
Figure 9F:
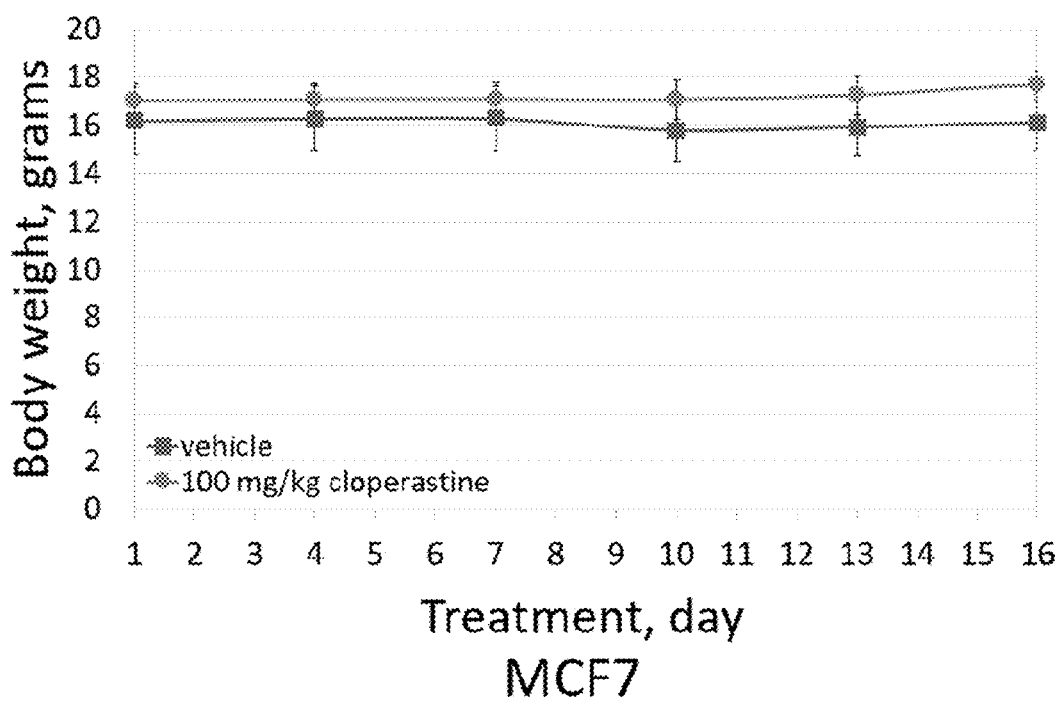
Figure 10A:
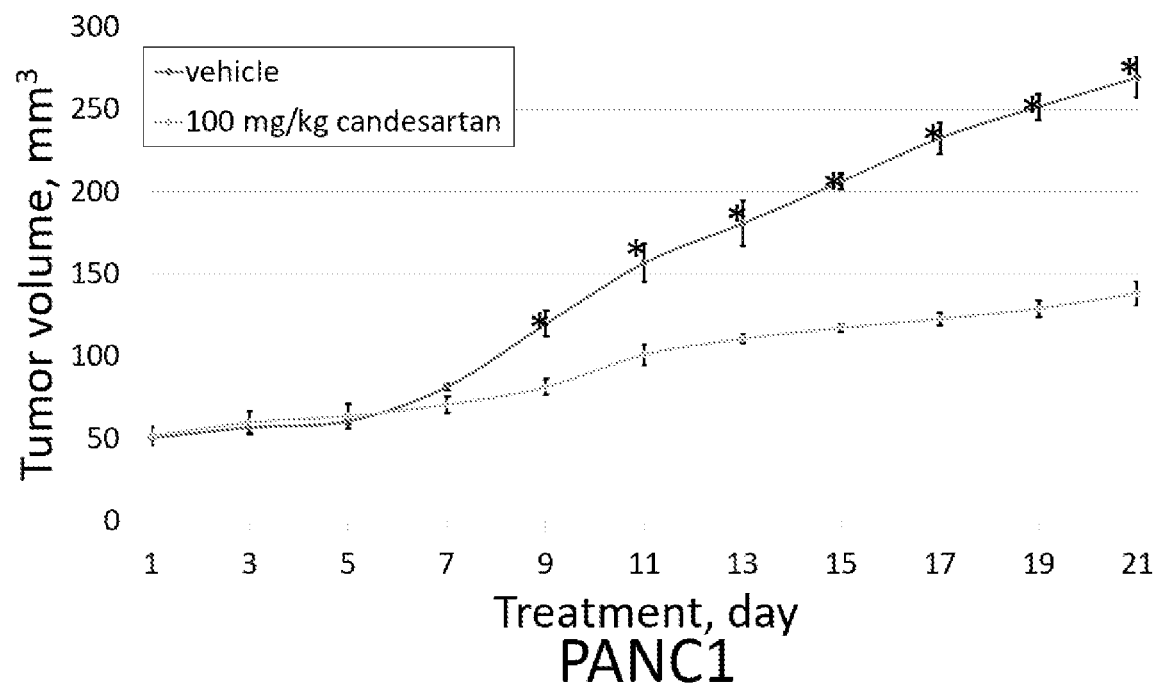
FIGS. 10A-10F provide data demonstrating how Can inhibits tumor growth in different in vivo mice cancer models.
Figure 10B:
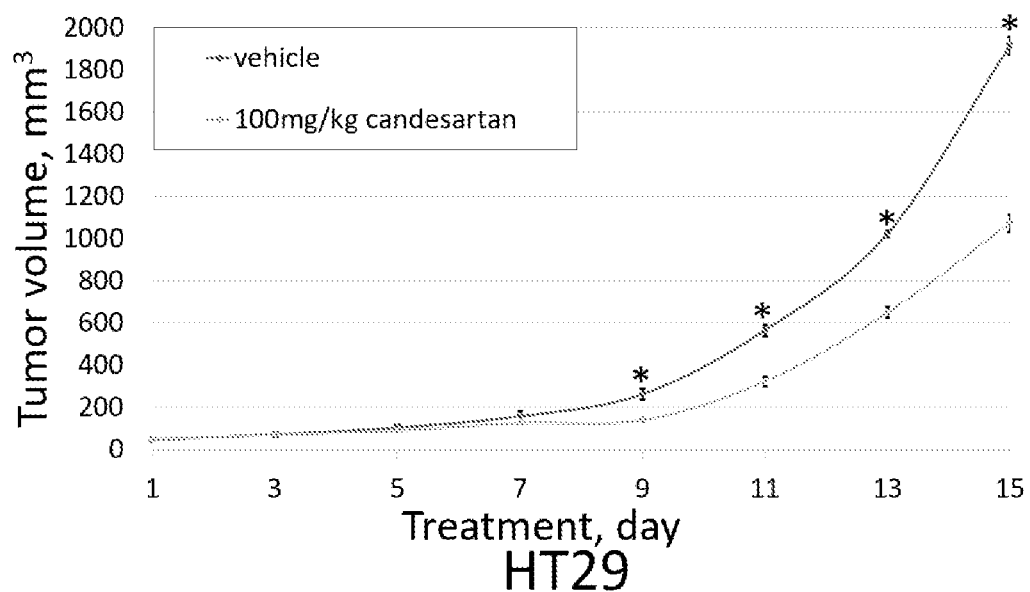
Figure 10C:
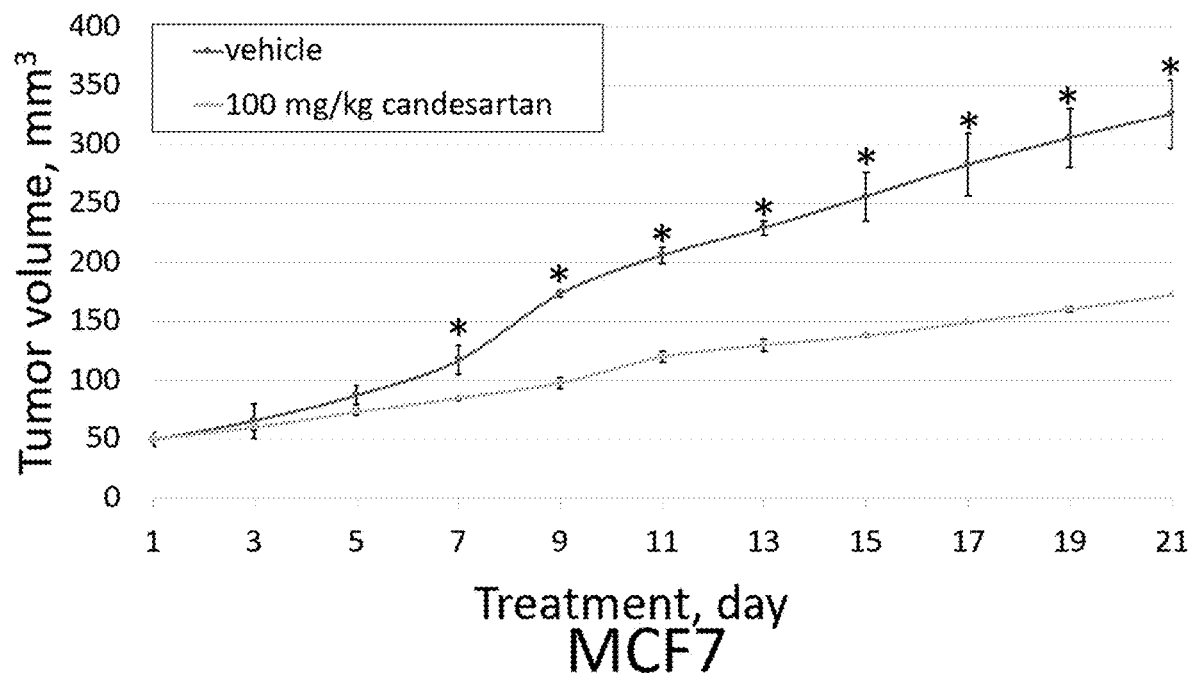
Figure 10D:
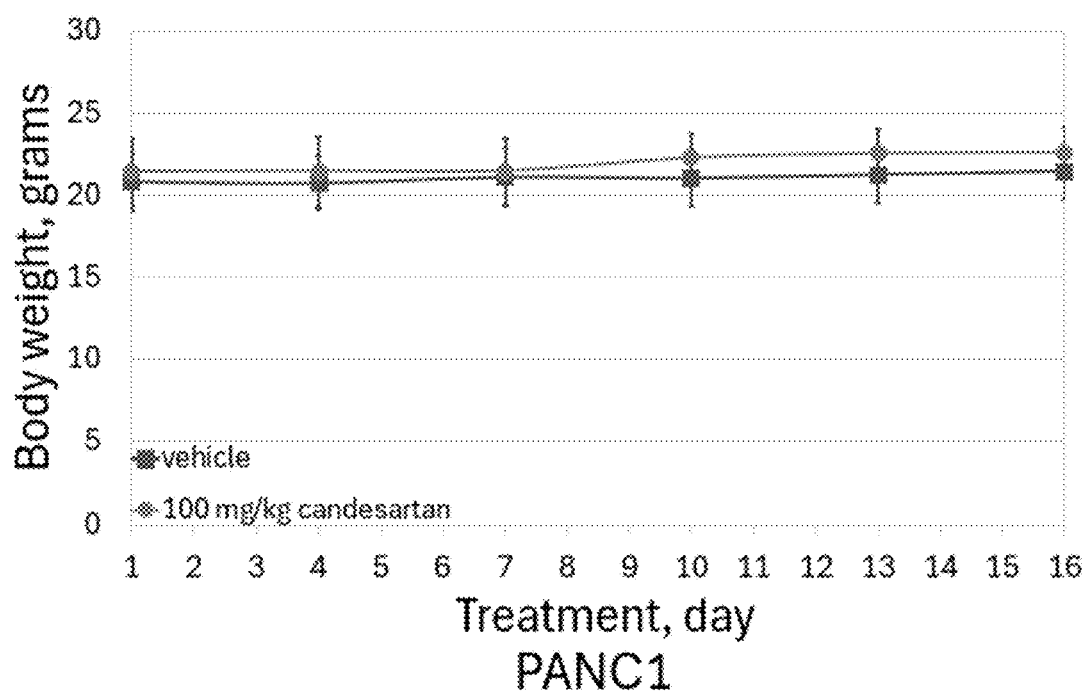
Figure 10E:
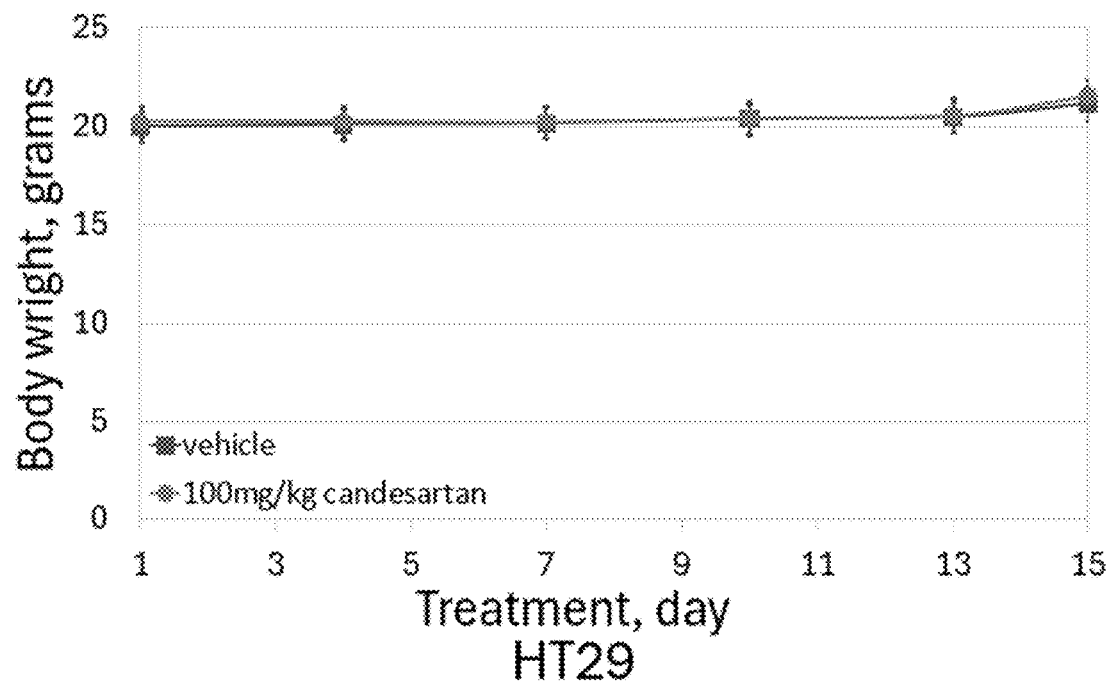
Figure 10F:
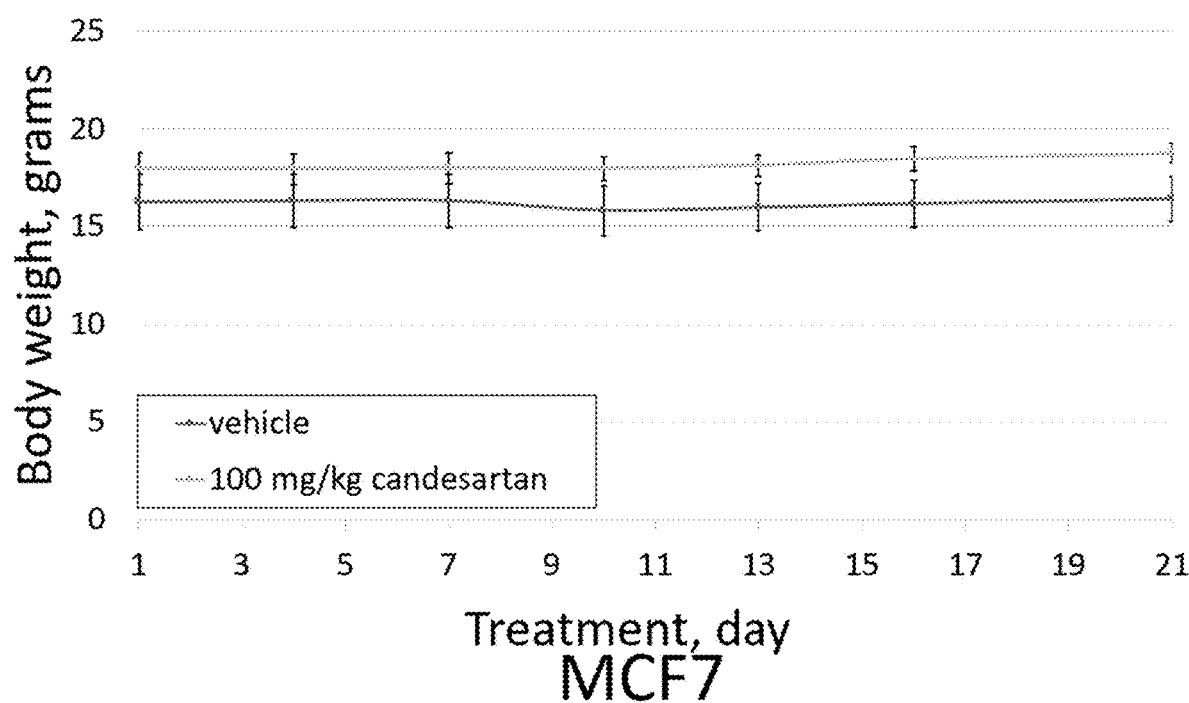

As shown in FIGS. 9A-9C, mice treated with Clo have significantly reduced tumor sizes over time relative to control mice. FIGS. 9D-9F demonstrate that body weights remained similar over the course of treatment in both Clo treated mice and control mice. Similarly, as shown in FIGS. 10A-10C, mice treated with Can have remarkably reduced tumor sizes over time relative to control mice. FIGS. 10D-10F demonstrate that body weights remained similar over the course of treatment in both Can treated mice and control mice.

In the past decades, the cost of drug development process has remained sky-high. From early discovery to the time a drug is approved for use in the clinic, it costs about a billion dollars and takes a total of 12-15 years. This is quite astounding as diseases such as cancer continue to rise at a rapid pace with each passing year. It is estimated that cancer will overtake heart disease to become the number one cause of disease-related deaths in US in the upcoming decade. The cost of treatment also continues to rise to counterbalance billions of dollars invested in drug development, thereby increasing the brunt on cancer patients. It is imperative to devise cost and time-effective strategies that help to find better treatment options for this deadly disease.

A strategy of identifying drugs already approved for certain indications by FDA and repurposing them to be used in three of the deadliest cancers that currently exist was developed: PDAC, CRC and BC. This strategy of repositioning approved drugs has been successfully used in the past to accelerate identification of new indications. Specifically, in the cancer field, a successful example of drug repurposing is Everolimus, which was originally identified as an immunosuppressant and later repurposed to be used in a rare form of advanced pancreatic neuroendocrine tumors. This and other examples fueled efforts to identify FDA-approved drugs to be repurposed for cancer by selectively inhibiting PRMT5 activity.

Figure 11:
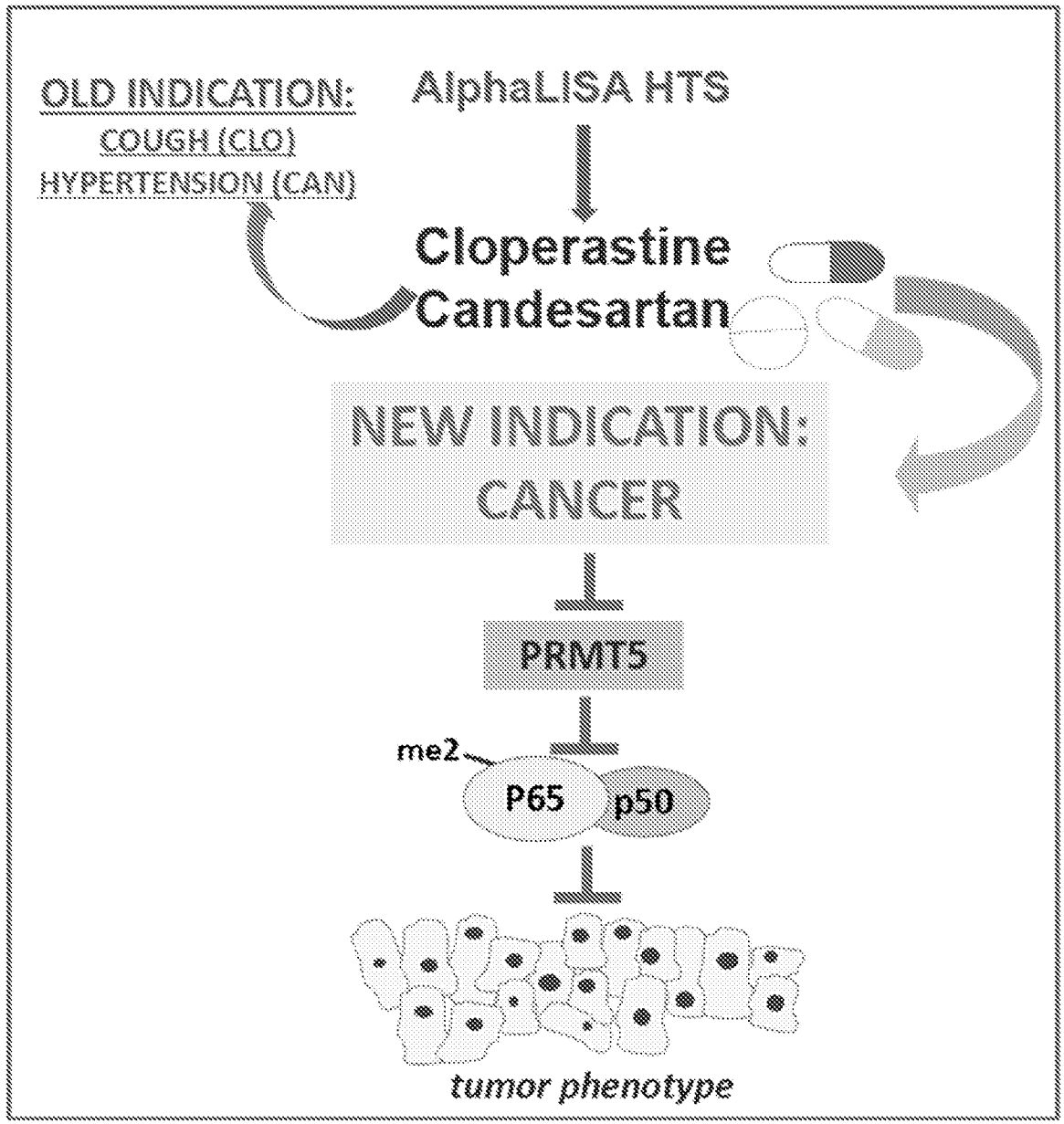
FIG. 11 illustrates the experimental approach of employing AlphaLISA HTS to identify two FDA-approved drugs, Clo and Can. Both drugs can be use in new indications via their ability to inhibit PRMT5 in cancer cells, such as PDAC, CRC and BC cells and in turn, inhibit the activation of its critical substrate, NF-κB, a known tumor promoter and provide a new therapeutic treatment for cancer patients.

PRMT5 has emerged as one of the most pursued targets in recent times. Indeed, a slew of latest drug discovery efforts have identified small molecule inhibitors against PRMT5. However, it will be at least a decade before these small molecules come close to clinical use as they have to navigate the drug approval process. Repurposing FDA-approved drugs instead seems like a lucrative option in comparison to this method. Furthermore, the wide interest in PRMT5 as a therapeutic target can be attributed to numerous studies identifying its contributions in promoting the cancer phenotype, including PDAC, CRC and BC. PRMT5 promotes cell proliferation, migratory ability, 3D colony formation ability, as well as activation of substrates via its methyltransferase activity. Additionally, activation of these substrates themselves may play a critical role in cancer. One such substrate is NF-κB. NF-κB is a well-established tumor promoter and contributes to chronic inflammatory responses and resistance to chemotherapy via its constitutive activation in cancer microenvironment. Two FDA-approved drugs were highlighted, Clo and Can identified using HTS that not only reduced cell proliferation, 3D colony growth, and mouse xenograft tumor growth in PDAC, CRC and BC, but also correlated at least partly via reduction of NF-κB activation. These results bring forth the promise of repositioning these FDA approved drugs as a treatment option in PDAC, CRC and BC, by selectively inhibiting PRMT5 and its tumor-promoting substrates (FIG. 11).

Various modifications and additions can be made to the embodiments disclosed herein without departing from the scope of the disclosure. For example, while the embodiments described above refer to particular features, the scope of this disclosure also includes embodiments having different combinations of features and embodiments that do not include all of the described features. Thus, the scope of the present disclosure is intended to embrace all such alternatives, modifications, and variations as fall within the scope of the claims, together with all equivalents. All publications, patents and patent applications referenced herein are hereby incorporated by reference in their entirety for all purposes as if each such publication, patent or patent application had been individually indicated to be incorporated by reference.

The invention claimed is:

1. A method of inhibiting an arginine methyltransferase (RMT), the method comprising the step of:
   contacting said arginine methyltransferase with a compound selected from the group consisting of cloperastine hydrochloride, candesartan cilexetil and arginine methyltransferase inhibiting analogs of cloperastine hydrochloride and candesartan cilexetil.

2. The method of claim 1 wherein said arginine methyltransferase is contacted with both cloperastine hydrochloride and candesartan cilexetil.

3. The method of claim 1 wherein said arginine methyltransferase is contacted with a composition comprising cloperastine hydrochloride and candesartan cilexetil.

4. The method of claim 1 wherein said arginine methyltransferase is first contacted with cloperastine hydrochloride or candesartan cilexetil and then subsequently contacted with the alternative compound not used in the first contact.

5. The method of claim 1 wherein said contact takes place in a cell.

6. The method of claim 5 wherein a patient is administered a pharmaceutical composition comprising a compound selected from the group consisting of cloperastine hydrochloride, and candesartan cilexetil.

7. The method of claim 6 wherein said patient is administered a pharmaceutical composition comprising cloperastine hydrochloride and a pharmaceutical composition comprising candesartan cilexetil, wherein there is a temporal delay between administering the cloperastine hydrochloride and candesartan cilexetil pharmaceutical compositions.

8. The method of claim 7 wherein the temporal delay is selected from 1 hour, 12 hours, 24 hours, 2 days, 3 days, 4 days, 5 days, 6 days, 1 week, 2 weeks and 1 month.

9. A method according to claim 1, where the arginine methyl transferase is protein arginine methyltransferase 5 (PRMT5).

10. A pharmaceutical composition comprising
   cloperastine hydrochloride;
   candesartan cilexetil; and
   a pharmaceutical acceptable carrier.

11. The pharmaceutical composition of claim 10 wherein the composition further comprises an antitumor agent.

12. The pharmaceutical composition of claim 11 wherein the antitumor agent is selected from the group consisting of Cyclophosphamide, Temozolomide, 5-fluorouracil (5-FU), 6-mercaptopurine (6-MP), Capecitabine, Gemcitabine, Dactinomycin, Bleomycin, Daunorubicin, Doxorubicin, Etoposide, Irinotecan, Topotecan, Docetaxel, Eribulin, Ixabepilone, Paclitaxel, Vinblastine, Albumin-bound paclitaxel (nab-paclitaxel), Eribulin, Liposomal doxorubicin, Mitoxantrone, Platinum, Vinorelbine, Oxaliplatin, Trifluridine, tipiracil, Bevacizumab, Irinotecan Hydrochloride, Cetuximab, Ramucirumab, Ipilimumab, Pembrolizumab, Leucovorin Calcium, Nivolumab, Panitumumab, Regorafenib, and Ziv-Aflibercept, or any combination thereof.

13. The pharmaceutical composition of claim 11 further comprising an immune checkpoint inhibitor, optionally wherein the checkpoint inhibitor is a PD-1 inhibitor, a PD-L1 inhibitor, or any combination thereof.

14. The pharmaceutical composition of claim 11 wherein the composition comprises a combination of antitumor agents selected from the following combination:
   Doxorubicin and Cyclophosphamide;
   Doxorubicin and Docetaxel;
   Cyclophosphamide, methotrexate, and fluorouracil;
   Fluorouracil, doxorubicin, and cyclophosphamide; or
   Cyclophosphamide, doxorubicin, and fluorouracil.

15. The pharmaceutical composition of claim 11 wherein the antitumor agent is a chemotherapeutic agent.

16. The pharmaceutical composition of claim 13, wherein the PD-1 inhibitor is pembrolizumab.

17. The pharmaceutical composition of claim 13, wherein the PD-L1 inhibitor is atezolizumab.

* * * * *